(12) United States Patent
Weitz et al.

(10) Patent No.: US 10,221,437 B2
(45) Date of Patent: Mar. 5, 2019

(54) ASSAYS AND OTHER REACTIONS INVOLVING DROPLETS

(71) Applicant: President and Fellows of Harvard College, Cambridge, MA (US)

(72) Inventors: David A. Weitz, Bolton, MA (US);
Jeremy Agresti, Richmond, CA (US);
Liang-Yin Chu, Chengdu (CN);
Jin-Woong Kim, Gyeonggi-do (KR);
Amy Rowat, Cambridge, MA (US);
Morten Sommer, Boston, MA (US);
Gautam Dantas, Allston, MA (US);
George Church, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/884,215

(22) Filed: Jan. 30, 2018

(65) Prior Publication Data
US 2018/0171373 A1    Jun. 21, 2018

Related U.S. Application Data

(63) Continuation of application No. 15/670,977, filed on Aug. 7, 2017, which is a continuation of application No. 15/449,637, filed on Mar. 3, 2017, now Pat. No. 9,816,121, which is a continuation of application No. 14/721,558, filed on May 26, 2015, now Pat. No. 9,850,526, which is a continuation of application No. 14/172,326, filed on Feb. 4, 2014, now Pat. No. 9,068,210, which is a continuation of application No. 12/529,926, filed as application No. PCT/US2008/003185 on Mar. 7, 2008, now Pat. No. 9,029,085.

(60) Provisional application No. 60/905,567, filed on Mar. 7, 2007.

(51) Int. Cl.

| | |
|---|---|
| C12P 19/34 | (2006.01) |
| C12Q 1/68 | (2018.01) |
| B01F 13/00 | (2006.01) |
| B01F 3/08 | (2006.01) |
| B01J 13/00 | (2006.01) |
| C12Q 1/686 | (2018.01) |
| C12Q 1/6848 | (2018.01) |
| C12Q 1/6834 | (2018.01) |
| G01N 15/14 | (2006.01) |
| B01L 3/00 | (2006.01) |
| G01N 15/10 | (2006.01) |

(52) U.S. Cl.
CPC .............. *C12P 19/34* (2013.01); *B01F 3/0811* (2013.01); *B01F 13/0062* (2013.01); *B01F 13/0071* (2013.01); *B01J 13/0052* (2013.01); *B01J 13/0065* (2013.01); *C12Q 1/686* (2013.01); *C12Q 1/6834* (2013.01); *C12Q 1/6848* (2013.01); *G01N 15/1404* (2013.01); *B01F 3/0807* (2013.01); *B01F 2215/0037* (2013.01); *B01L 3/502784* (2013.01); *G01N 2015/1006* (2013.01)

(58) Field of Classification Search
CPC .... C12P 19/34; B01F 13/0071; C12Q 1/6834; C12Q 2563/159
See application file for complete search history.

(56) References Cited

U.S. PATENT DOCUMENTS

| | | | |
|---|---|---|---|
| 5,149,625 | A | 9/1992 | Church et al. |
| 5,202,231 | A | 4/1993 | Drmanac et al. |
| 5,436,130 | A | 7/1995 | Mathies et al. |
| 5,512,131 | A | 4/1996 | Kumar et al. |
| 5,695,940 | A | 12/1997 | Drmanac et al. |
| 5,736,330 | A | 4/1998 | Fulton |
| 5,834,252 | A | 11/1998 | Stemmer et al. |

(Continued)

FOREIGN PATENT DOCUMENTS

| | | |
|---|---|---|
| EP | 0 249 007 A2 | 12/1987 |
| EP | 1 019 496 B1 | 9/2004 |

(Continued)

OTHER PUBLICATIONS

PCT/US2008/003185, Oct. 22, 2008, Invitation to Pay Additional Fees.

(Continued)

*Primary Examiner* — David C Thomas
(74) *Attorney, Agent, or Firm* — Wolf, Greenfield & Sacks, P.C.

(57) ABSTRACT

The present invention generally relates to droplets and/or emulsions, such as multiple emulsions. In some cases, the droplets and/or emulsions may be used in assays, and in certain embodiments, the droplet or emulsion may be hardened to form a gel. In some aspects, a heterogeneous assay can be performed using a gel. For example, a droplet may be hardened to form a gel, where the droplet contains a cell, DNA, or other suitable species. The gel may be exposed to a reactant, and the reactant may interact with the gel and/or with the cell, DNA, etc., in some fashion. For example, the reactant may diffuse through the gel, or the hardened particle may liquefy to form a liquid state, allowing the reactant to interact with the cell. As a specific example, DNA contained within a gel particle may be subjected to PCR (polymerase chain reaction) amplification, e.g., by using PCR primers able to bind to the gel as it forms. As the DNA is amplified using PCR, some of the DNA will be bound to the gel via the PCR primer. After the PCR reaction, unbound DNA may be removed from the gel, e.g., via diffusion or washing. Thus, a gel particle having bound DNA may be formed in one embodiment of the invention.

62 Claims, 5 Drawing Sheets

Specification includes a Sequence Listing.

(56) References Cited

U.S. PATENT DOCUMENTS

| | | | |
|---|---|---|---|
| 5,851,769 A | 12/1998 | Gray et al. |
| 6,046,003 A | 4/2000 | Mandecki |
| 6,051,377 A | 4/2000 | Mandecki |
| 6,057,107 A | 5/2000 | Fulton |
| 6,103,537 A | 8/2000 | Ullman et al. |
| 6,297,006 B1 | 10/2001 | Drmanac et al. |
| 6,297,017 B1 | 10/2001 | Schmidt et al. |
| 6,355,198 B1 | 3/2002 | Kim et al. |
| 6,361,950 B1 | 3/2002 | Mandecki |
| 6,432,360 B1 | 8/2002 | Church |
| 6,485,944 B1 | 11/2002 | Church et al. |
| 6,511,803 B1 | 1/2003 | Church et al. |
| 6,524,456 B1 | 2/2003 | Ramsey et al. |
| 6,586,176 B1 | 7/2003 | Trnovsky et al. |
| 6,632,606 B1 | 10/2003 | Ullman et al. |
| 6,670,133 B2 | 12/2003 | Knapp et al. |
| 6,767,731 B2 | 7/2004 | Hannah |
| 6,800,298 B1 | 10/2004 | Burdick et al. |
| 6,806,058 B2 | 10/2004 | Jesperson et al. |
| 6,913,935 B1 | 7/2005 | Thomas |
| 6,929,859 B2 | 8/2005 | Chandler et al. |
| 7,041,481 B2 | 5/2006 | Anderson et al. |
| 7,129,091 B2 | 10/2006 | Ismagilov et al. |
| 7,268,167 B2 | 9/2007 | Higuchi et al. |
| 7,425,431 B2 | 9/2008 | Church et al. |
| 7,536,928 B2 | 5/2009 | Kazuno |
| 7,604,938 B2 | 10/2009 | Takahashi et al. |
| 7,638,276 B2 | 12/2009 | Griffiths et al. |
| 7,708,949 B2 | 5/2010 | Stone et al. |
| RE41,780 E | 9/2010 | Anderson et al. |
| 7,799,553 B2 | 9/2010 | Mathies et al. |
| 7,968,287 B2 | 6/2011 | Griffiths et al. |
| 8,252,539 B2 | 8/2012 | Quake et al. |
| 8,273,573 B2 | 9/2012 | Ismagilov et al. |
| 8,278,071 B2 | 10/2012 | Brown et al. |
| 8,304,193 B2 | 11/2012 | Ismagilov et al. |
| 8,329,407 B2 | 12/2012 | Ismagilov et al. |
| 8,748,094 B2 | 6/2014 | Weitz et al. |
| 8,748,102 B2 | 6/2014 | Berka et al. |
| 8,765,380 B2 | 7/2014 | Berka et al. |
| 8,822,148 B2 | 9/2014 | Ismagilov et al. |
| 8,871,444 B2 | 10/2014 | Griffiths et al. |
| 8,889,083 B2 | 11/2014 | Ismagilov et al. |
| 9,017,948 B2 | 4/2015 | Agresti et al. |
| 9,029,083 B2 | 5/2015 | Griffiths et al. |
| 9,029,085 B2 | 5/2015 | Agresti et al. |
| 9,068,210 B2 | 6/2015 | Agresti et al. |
| 9,797,010 B2 | 10/2017 | Weitz et al. |
| 9,816,121 B2 | 11/2017 | Agresti et al. |
| 9,850,526 B2 | 12/2017 | Agresti et al. |
| 2001/0020588 A1 | 9/2001 | Adourian et al. |
| 2001/0044109 A1 | 11/2001 | Mandecki |
| 2002/0034737 A1 | 3/2002 | Drmanac |
| 2002/0034747 A1 | 3/2002 | Bruchez et al. |
| 2002/0051992 A1 | 5/2002 | Bridgham et al. |
| 2002/0058332 A1 | 5/2002 | Quake et al. |
| 2002/0092767 A1 | 7/2002 | Bjornson et al. |
| 2002/0179849 A1 | 12/2002 | Maher et al. |
| 2003/0008285 A1 | 1/2003 | Fischer |
| 2003/0008323 A1 | 1/2003 | Ravkin et al. |
| 2003/0028981 A1 | 2/2003 | Chandler et al. |
| 2003/0039978 A1 | 2/2003 | Hannah |
| 2003/0044777 A1 | 3/2003 | Beattie |
| 2003/0044836 A1 | 3/2003 | Levine et al. |
| 2003/0099954 A1 | 5/2003 | Miltenyi et al. |
| 2003/0104466 A1 | 6/2003 | Knapp et al. |
| 2003/0108897 A1 | 6/2003 | Drmanac |
| 2003/0170698 A1 | 9/2003 | Gascoyne et al. |
| 2003/0182068 A1 | 9/2003 | Battersby et al. |
| 2003/0207260 A1 | 11/2003 | Trnovsky et al. |
| 2003/0215862 A1 | 11/2003 | Parce et al. |
| 2004/0063138 A1 | 4/2004 | McGinnis et al. |
| 2004/0132122 A1 | 7/2004 | Banerjee et al. |
| 2005/0019839 A1 | 1/2005 | Jesperson et al. |
| 2005/0042625 A1 | 2/2005 | Schmidt et al. |
| 2005/0136486 A1 | 6/2005 | Haushalter |
| 2005/0153290 A1 | 7/2005 | Van Beuningen et al. |
| 2005/0172476 A1 | 8/2005 | Stone et al. |
| 2005/0181379 A1 | 8/2005 | Su et al. |
| 2005/0221339 A1 | 10/2005 | Griffiths et al. |
| 2005/0244850 A1 | 11/2005 | Huang et al. |
| 2005/0287572 A1 | 12/2005 | Mathies et al. |
| 2006/0020371 A1 | 1/2006 | Ham et al. |
| 2006/0073487 A1 | 4/2006 | Oliver et al. |
| 2006/0078888 A1 | 4/2006 | Griffiths et al. |
| 2006/0153924 A1 | 7/2006 | Griffiths et al. |
| 2006/0163385 A1 | 7/2006 | Link et al. |
| 2006/0240506 A1 | 10/2006 | Kushmaro et al. |
| 2006/0257893 A1 | 11/2006 | Takahashi et al. |
| 2006/0292583 A1 | 12/2006 | Schneider et al. |
| 2007/0003442 A1 | 1/2007 | Link et al. |
| 2007/0020617 A1 | 1/2007 | Trnovsky et al. |
| 2007/0054119 A1 | 3/2007 | Garstecki et al. |
| 2007/0092914 A1 | 4/2007 | Griffiths et al. |
| 2007/0172873 A1 | 7/2007 | Brenner et al. |
| 2007/0195127 A1 | 8/2007 | Ahn et al. |
| 2007/0228588 A1 | 10/2007 | Noritomi et al. |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2009/0012187 A1 | 1/2009 | Chu et al. |
| 2009/0035770 A1 | 2/2009 | Mathies et al. |
| 2009/0068170 A1 | 3/2009 | Weitz et al. |
| 2009/0131543 A1 | 5/2009 | Weitz et al. |
| 2009/0197248 A1 | 8/2009 | Griffiths et al. |
| 2009/0197772 A1 | 8/2009 | Griffiths et al. |
| 2009/0286687 A1 | 11/2009 | Dressman et al. |
| 2010/0022414 A1 | 1/2010 | Link et al. |
| 2010/0130369 A1 | 5/2010 | Shenderov et al. |
| 2010/0136544 A1 | 6/2010 | Agresti et al. |
| 2010/0137163 A1 | 6/2010 | Link et al. |
| 2010/0173394 A1 | 7/2010 | Colston, Jr. et al. |
| 2010/0210479 A1 | 8/2010 | Griffiths et al. |
| 2011/0086780 A1 | 4/2011 | Colston et al. |
| 2011/0092392 A1 | 4/2011 | Colston et al. |
| 2011/0160078 A1 | 6/2011 | Fodor et al. |
| 2011/0218123 A1 | 9/2011 | Weitz et al. |
| 2011/0267457 A1 | 11/2011 | Weitz et al. |
| 2012/0010098 A1 | 1/2012 | Griffiths et al. |
| 2012/0010107 A1 | 1/2012 | Griffiths et al. |
| 2012/0015382 A1 | 1/2012 | Weitz et al. |
| 2012/0015822 A1 | 1/2012 | Weitz et al. |
| 2012/0190032 A1 | 7/2012 | Ness et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2013/0079231 A1 | 3/2013 | Pushkarev et al. |
| 2013/0109575 A1 | 5/2013 | Kleinschmidt et al. |
| 2013/0157899 A1 | 6/2013 | Adler et al. |
| 2013/0210639 A1 | 8/2013 | Link et al. |
| 2013/0274117 A1 | 10/2013 | Church et al. |
| 2014/0155295 A1 | 6/2014 | Hindson et al. |
| 2014/0194323 A1 | 7/2014 | Gillevet |
| 2014/0199730 A1 | 7/2014 | Agresti et al. |
| 2014/0199731 A1 | 7/2014 | Agresti et al. |
| 2014/0227684 A1 | 8/2014 | Hindson et al. |
| 2014/0235506 A1 | 8/2014 | Hindson et al. |
| 2014/0303039 A1 | 10/2014 | Weitz et al. |
| 2014/0378349 A1 | 12/2014 | Hindson et al. |
| 2015/0005200 A1 | 1/2015 | Hindson et al. |
| 2015/0353999 A1 | 12/2015 | Agresti et al. |
| 2017/0183701 A1 | 6/2017 | Agresti et al. |
| 2017/0183715 A1 | 6/2017 | Weitz et al. |
| 2018/0023109 A1 | 1/2018 | Weitz et al. |
| 2018/0057875 A1 | 3/2018 | Weitz et al. |
| 2018/0119212 A1 | 5/2018 | Weitz et al. |

FOREIGN PATENT DOCUMENTS

| | | |
|---|---|---|
| EP | 1 482 036 B1 | 10/2007 |
| EP | 1 594 980 B1 | 11/2009 |
| EP | 1 967 592 B1 | 4/2010 |
| EP | 2 258 846 A2 | 12/2010 |

(56) References Cited

FOREIGN PATENT DOCUMENTS

| | | |
|---|---|---|
| EP | 2 145 955 B1 | 2/2012 |
| EP | 2145955 B1 | 2/2012 |
| EP | 1 905 828 B1 | 8/2012 |
| EP | 1905828 B1 | 8/2012 |
| EP | 1 908 832 B1 | 12/2012 |
| EP | 1908832 B1 | 12/2012 |
| EP | 2 540 389 B1 | 1/2013 |
| JP | S59-049832 A2 | 3/1984 |
| JP | 2004-361291 A | 12/2004 |
| JP | 2006-507921 A | 3/2006 |
| JP | 2006-289250 A | 10/2006 |
| JP | 2007-268350 A | 10/2007 |
| JP | 2007-298327 A | 11/2007 |
| JP | 2009-208074 A2 | 9/2009 |
| WO | WO 96/29629 A2 | 9/1996 |
| WO | WO 96/41011 A1 | 12/1996 |
| WO | WO 99/09217 A1 | 2/1999 |
| WO | WO 99/52708 A1 | 10/1999 |
| WO | WO 00/08212 A1 | 2/2000 |
| WO | WO 00/26412 A1 | 5/2000 |
| WO | WO 00/50172 A1 | 8/2000 |
| WO | WO 00/56937 A2 | 9/2000 |
| WO | WO 01/14589 A2 | 3/2001 |
| WO | WO 01/89787 A2 | 11/2001 |
| WO | WO 02/31203 A2 | 4/2002 |
| WO | WO 02/086148 A1 | 10/2002 |
| WO | WO 2004/002627 A2 | 1/2004 |
| WO | WO 2004/087308 A1 | 10/2004 |
| WO | WO 2004/088314 A1 | 10/2004 |
| WO | WO 2004/091763 A2 | 10/2004 |
| WO | WO 2004/102204 A1 | 11/2004 |
| WO | WO 2004/103565 A2 | 12/2004 |
| WO | WO 2005/021151 A1 | 3/2005 |
| WO | WO 2005/040406 A1 | 5/2005 |
| WO | WO 2005/049787 A2 | 6/2005 |
| WO | WO 2005/082098 A2 | 9/2005 |
| WO | WO 2006/078841 A1 | 7/2006 |
| WO | WO 2006/096571 A2 | 9/2006 |
| WO | WO 2007/001448 A2 | 1/2007 |
| WO | WO 2007/002490 A2 | 1/2007 |
| WO | WO 2007/024840 A2 | 3/2007 |
| WO | WO 2007/081385 A2 | 7/2007 |
| WO | WO 2007/081387 A1 | 7/2007 |
| WO | WO 2007/089541 A2 | 8/2007 |
| WO | WO 2007/114794 A1 | 10/2007 |
| WO | WO 2007/121489 A2 | 10/2007 |
| WO | WO 2007/133710 A2 | 11/2007 |
| WO | WO 2007/138178 A2 | 12/2007 |
| WO | WO 2007/139766 A2 | 12/2007 |
| WO | WO 2007/140015 A2 | 12/2007 |
| WO | WO 2007/149432 A2 | 12/2007 |
| WO | WO 2008/021123 A1 | 2/2008 |
| WO | WO 2008/091792 A2 | 7/2008 |
| WO | WO 2008/102057 A1 | 8/2008 |
| WO | WO 2008/109176 A2 | 9/2008 |
| WO | WO 2008/134153 A1 | 11/2008 |
| WO | WO 2009/005680 A1 | 1/2009 |
| WO | WO 2009/011808 A1 | 1/2009 |
| WO | WO 2009/085215 A1 | 7/2009 |
| WO | WO 2010/151776 A2 | 12/2010 |
| WO | WO 2011/056546 A1 | 5/2011 |
| WO | WO 2012/048341 A1 | 4/2012 |
| WO | WO 2013/177220 A1 | 11/2013 |

OTHER PUBLICATIONS

PCT/US2008/003185, Jan. 12, 2009, International Search Report and Written Opinion.
PCT/US2008/003185, Sep. 17, 2009, International Preliminary Report on Patentability.
PCT/US2008/008563, Oct. 29, 2008, International Search Report and Written Opinion.
CN 200880127116.4, Jun. 18, 2012, Office Action.
CN 200880127116.4, May 23, 2013, Office Action.
CN 200880127116.4, Dec. 24, 2013, Office Action.
EP 08865992.5, Dec. 15, 2010, Office Communication.
EP 08865992.5, Jan. 23, 2012, Office Communication.
EP 08865992.5, Apr. 5, 2013, Office Communication.
EP 08865992.5, Aug. 29, 2013, Office Communication.
EP 08865992.5, Apr. 29, 2014, Office Communication.
JP 2010-539498, Jul. 17, 2013, Office Action.
JP 2010-539498, Sep. 2, 2014, Office Action.
PCT/US2008/013912, Apr. 3, 2009, International Search Report and Written Opinion.
PCT/US2008/013912, Jul. 1, 2010, International Preliminary Report on Patentability.
PCT/US2009/005184, May 27, 2010, Invitation to Pay Additional Fees.
PCT/US2009/005184, Aug. 16, 2010, International Search Report and Written Opinion.
PCT/US2009/005184, Mar. 31, 2011, International Preliminary Report on Patentability.
PCT/US2009/003389, Oct. 21, 2009, International Search Report and Written Opinion.
PCT/US2009/004037, Oct. 2, 2009, International Search Report and Written Opinion.
EP 9804166.8, Nov. 7, 2014, Office Action.
EP 16197694.9, Feb. 9, 2017, Extended European Search Report.
PCT/US2009/006649, Mar. 10, 2010, International Search Report and Written Opinion.
PCT/US2009/006649, Jun. 30, 2011, International Preliminary Report on Patentability.
AU 2010315580, Dec. 17, 2013, Office Action.
CN 201080055990.9, Dec. 16, 2013, Office Action.
CN 201080055990.9, Jul. 30, 2014, Office Action.
CN 201080055990.9, Jan. 22, 2015, Chinese Office Action.
CN 201080055990.9, Jul. 7, 2015, Chinese Office Action.
JP 2012-536941, Nov. 19, 2013, Japanese Office Action.
JP 2012-536941, Aug. 5, 2014, Japanese Office Action.
PCT/US2010/054050, Jan. 31, 2011, International Search Report and Written Opinion.
PCT/US2010/054050, May 10, 2012, International Preliminary Report on Patentability.
Office Action dated Oct. 1, 2012 for U.S. Appl. No. 12/529,926.
Final Office Action dated May 28, 2013 for U.S. Appl. No. 12/529,926.
Interview Summary dated Feb. 12, 2014 for U.S. Appl. No. 12/529,926.
Office Action dated Aug. 6, 2014 for U.S. Appl. No. 12/529,926.
Office Action dated May 20, 2014 for U.S. Appl. No. 14/172,266.
Final Office Action dated Nov. 21, 2014 for U.S. Appl. No. 14/172,266.
Advisory Action dated Jan. 23, 2015 for U.S. Appl. No. 14/172,266.
Office Action dated May 20, 2014 for U.S. Appl. No. 14/172,326.
Final Office Action dated Nov. 20, 2014 for U.S. Appl. No. 14/172,326.
Advisory Action dated Jan. 23, 2015 for U.S. Appl. No. 14/172,326.
Office Action dated Feb. 13, 2017 for U.S. Appl. No. 14/721,558.
Office Action dated May 15, 2017 for U.S. Appl. No. 14/721,558.
Office Action dated Jul. 30, 2014 for U.S. Appl. No. 12/809,120.
Office Action dated Mar. 12, 2015 for U.S. Appl. No. 12/809,120.
Advisory Action dated Jun. 25, 2015 for U.S. Appl. No. 12/809,120.
Office Action dated Mar. 29, 2016 for U.S. Appl. No. 12/809,120.
Office Action dated Jul. 20, 2016 for U.S. Appl. No. 12/809,120.
Office Action dated May 26, 2017 for U.S. Appl. No. 12/809,120.
Notice of Allowance dated Jul. 11, 2017 for U.S. Appl. No. 12/809,120.
Office Action dated Apr. 24, 2013 for U.S. Appl. No. 13/119,470.
Final Office Action dated Dec. 5, 2013 for U.S. Appl. No. 13/119,470.
Advisory Action dated Mar. 21, 2014 for U.S. Appl. No. 13/119,470.
Office Action dated Jun. 24, 2015 for U.S. Appl. No. 13/119,470.
Office Action dated Feb. 28, 2013 for U.S. Appl. No. 13/139,326.
Final Office Action dated Aug. 6, 2013 for U.S. Appl. No. 13/139,326.
Advisory Action dated Nov. 20, 2013 for U.S. Appl. No. 13/139,326.
Notice of Allowance dated Jan. 27, 2014 for U.S. Appl. No. 13/139,326.
Office Action dated Jan. 6, 2016 for U.S. Appl. No. 14/262,895.
Office Action dated Apr. 27, 2016 for U.S. Appl. No. 14/262,895.
Advisory Action dated Aug. 10, 2016 for U.S. Appl. No. 14/262,895.

(56) References Cited

OTHER PUBLICATIONS

Advisory Action dated Nov. 25, 2016 for U.S. Appl. No. 14/262,895.
Office Action dated Sep. 17, 2013 for U.S. Appl. No. 13/503,588.
Office Action dated Feb. 10, 2014 for U.S. Appl. No. 13/503,588.
Advisory Action dated May 16, 2014 for U.S. Appl. No. 13/503,588.
Invitation to Pay Additional Fees for PCT/US2008/003185 dated Oct. 22, 2008.
International Search Report and Written Opinion of the International Searching Authority for International Application No. PCT/US2008/003185, dated Jan. 12, 2009.
International Preliminary Report on Patentability for PCT/US2008/003185 dated Sep. 17, 2009.
International Search Report and Written Opinion of the International Searching Authority for International Application No. PCT/US2008/008563, dated Oct. 29, 2008.
Chinese Office Action dated Jun. 18, 2012 for CN Application No. 200880127116.4.
Chinese Office Action dated May 23, 2013 for Application No. CN 200880127116.4.
Chinese Office Action dated Dec. 24, 2013 for CN Application No. 200880127116.4.
Office Communication dated Dec. 15, 2010 for Application No. EP 08865992.5.
Office Communication dated Jan. 23, 2012 for Application No. EP 08865992.5
Office Communication dated Apr. 5, 2013 for Application No. EP 08865992.5.
Office Communication dated Aug. 29, 2013 for Application No. EP 08865992.5.
Office Communication dated Apr. 29, 2014 for EP Application No. EP 08865992.5.
Japanese Office Action dated Jul. 17, 2013 for Application No. JP 2010-539498.
Japanese Office Action dated Sep. 2, 2014 for Application No. JP 2010-539498.
International Search Report and Written Opinion of the International Searching Authority for International Application No. PCT/US2008/013912, dated Apr. 3, 2009.
International Preliminary Report on Patentability for PCT/US2008/013912 dated Jul. 1, 2010.
Invitation to Pay Additional Fees for PCT Application PCT/US09/005184 dated May 27, 2010.
International Search Report and Written Opinion from PCT Application PCT/US09/005184 dated Aug. 16, 2010.
International Preliminary Report on Patentability for PCT Application PCT/US09/005184 dated Mar. 31, 2011.
International Search Report and Written Opinion of the International Searching Authority for International Application No. PCT/US2009/003389, dated Oct. 21, 2009.
International Search Report and Written Opinion of the International Searching Authority for International Application No. PCT/US2009/004037, dated Oct. 2, 2009.
European Office action dated Nov. 7, 2014 for Application No. EP 09804166.8.
Extended European Search Report dated Feb. 9, 2017 for Application No. EP 16197694.9.
International Search Report and Written Opinion for International Application No. PCT/US2009/006649 dated Mar. 10, 2010.
International Preliminary Report on Patentability for International Application No. PCT/US2009/006649 dated Jun. 30, 2011.
Australian Office Action dated Dec. 17, 2013 for Application No. AU 2010315580.
Chinese Office Action dated Dec. 16, 2013 for Application No. CN 201080055990.9.
Chinese Office Action dated Jul. 30, 2014 for Application No. CN 201080055990.9.
Chinese Office Action dated Jan. 22, 2015 for Application No. CN 20108005990.9.
Chinese Office Action dated Jul. 7, 2015 for Application No. CN 201080055990.9.
Japanese Office Action dated Nov. 19, 2013 for Application No. JP 2012-536941.
Japanese Office Action dated Aug. 5, 2014 for Application No. JP 2012-536941.
International Search Report and Written Opinion from PCT Application PCT/US2010/054050 dated Jan. 31, 2011.
International Preliminary Report on Patentability from PCT Application PCT/US2010/054050 dated May 10, 2012.
[No Author] Gene Characterization Kits. Stratagene Catalog. Stratagene Cloning Systems: Tools and Technology for Lift Sciences. 1988. 3 pages.
[No Author] Microfluidic ChipShop. Microfluidic product catalogue. Mar. 2005.
[No Author] Microfluidic ChipShop. Microfluidic product catalogue. Oct. 2009.
Abate et al., Droplet Based Sequencing. American Physical Society. Presentation. Mar. 12, 2008. 25 pages.
Abate et al., Valve-based flow focusing for drog formation. Appl Phys Lett. 2009;94. 3 pages. (Month not cited on publication).
Agresti, "Selection of ribozymes that catalyse multiple-turnover Diels-Alder cycloadditions by using in vitro compartmentalization", PNAS, 102, 16170-16175 (2005). (Nov. 2005).
Akselband, "Enrichment of slow-growing marine microorganisms from mixed cultures using gel microdrop (GMD) growth assay and fluorescence-activated cell sorting", J. Exp. Marine Biol., 329: 196-205 (2006). (Month not cited on publication).
Akselband, "Rapid mycobacteria drug susceptibility testing using gel microdrop (GMD) growth assay and flow cytometry", J. Microbiol. Methods, 62:181-197 (2005). (Month not cited on publication).
Anna et al., Formation of dispersions using 'flow focusing' in microchannels. Appln Phys Letts. 2003;82(3):364-66. (Jan. 2003).
Boone, et al. Plastic advances microfluidic devices. The devices debuted in silicon and glass, but plastic fabrication may make them hugely successful in biotechnology application. Analytical Chemistry. Feb. 2002; 78A-86A.
Braeckmans et al., Scanning the Code. Modern Drug Discovery. 2003:28-32. (Feb. 2003).
Carroll, "The selection of high-producing cell lines using flow cytometry and cell sorting", Exp. Op. Biol. Therp., 4:11 1821-1829 (2004). (Month not cited on publication).
Chaudhary "A rapid method of cloning functional variable-region antibody genese in *Escherichia coli* as single-chain immunotoxins" Proc. Natl. Acad. Sci USA 87: 1066-1070 (Feb. 1990).
Chechetkin et al., Sequencing by hybridization with the generic 6-mer oligonucleotide microarray: an advanced scheme for data processing. J Biomol Struct Dyn. Aug. 2000;18(1):83-101. (Month not cited on publication).
Chou, et al. Disposable Microdevices for DNA Analysis and Cell Sorting. Proc. Solid-State Sensor and Actuator Workshop, Hilton Head, SC. Jun. 8-11, 1998; 11-14.
Chu, L., et al., "Controllable Monodisperse Multiple Emulsions," Angew. Chem. Int. Ed., vol. 46, pp. 8970-8974 (2007). (Month not cited on publication).
Clausell-Tormos et al., "Droplet-based microfluidic platforms for the encapsulation and screening of mammalian cells and multicellular organisms", Chem. Biol. 15:427-437 (2008). (May 2008).
De Bruin et al., UBS Investment Research. Q-Series®: DNA Sequencing. UBS Securities LLC. Jul. 12, 2007. 15 pages.
Diaz, R.V., et al., "One-Month sustained release microspheres of 125 I-bovine calcitonin In vitro-in vivo studies," Journal of Controlled Release, vol. 59, pp. 55-62 (1999). (Month not cited on publication).
Doerr, The smallest bioreactor. Nature Methods. 2005; 2(5):326. (May 2005).
Drmanac eta l., Sequencing by hybridization (SBH): advantages, achievements, and opportunities. Adv Biochem Eng Biotechnol. 2002;77:75-101. (Month not cited on publication).
Fu, "A microfabricated fluorescence-activated cell sorter", Nature Biotech., 17:1109-1111 (1999). (Nov. 1999).
Fulton et al., Advanced multiplexed analysis with the FlowMetrix system. Clin Chem. Sep. 1997;43(9):1749-56.

(56) References Cited

OTHER PUBLICATIONS

Gartner, et al. The Microfluidic Toolbox—examples for fluidic interfaces and standardization concepts. Proc. SPIE 4982, Microfluidics, BioMEMS, and Medical Microsystems, (Jan. 17, 2003); doi: 10.1117/12.479566.
Ghadessy et al. Directed evolution of polymerase function by compartmentalized self-replication. Proc Natl Acad Sci USA. Apr. 10, 2001; 98(8):4552-7. Epub Mar. 27, 2001.
Griffiths et al., Directed evolution of an extremely fast phosphotriesterase by in vitro compartmentalization. EMBO J. Jan. 2, 2003;22(1):24-35.
He et al., "Selective Encapsulation of Single Cells and Subcellular Organelles into Picoliter- and Femtoliter-Volume Droplets" Anal. Chem 77: 1539-1544 (2005) (Mar. 2005).
Holtze et al., Biocompatible surfactants for water-in-fluorocarbon emulsions. Lab Chip. Oct. 2008; 8(10):1632-9.
Huebner, "Quantitative detection of protein expression in single cells using droplet microfluidics", Chem. Commun. 1218-1220 (2007). (Month not cited on publication).
Hug et al. Measurement of the number of molecules of a single mRNA species in a complex mRNA preparation. J Theor Biol. Apr. 21, 2003; 221(4):615-24.
Khomiakova et al., [Analysis of perfect and mismatched DNA duplexes by a generic hexanucleotide microchip]. Mol Biol (Mosk). Jul.-Aug. 2003;37(4):726-41. Russian.
Kim et al., Fabrication of monodisperse gel shells and functional microgels in microfluidic devices. Angew Chem Int Ed Engl. Mar. 2007;46(11):1819-22.
Kim, "Fabrication of monodisperse gel shells and functional microgels in microfluidic devices", Angew. Chem., 119:1851-1854 (2007).
Kim, J., et al, "Albumin loaded microsphere of amphiphilic poly-(ethylene glycol)/poly(a-ester) multiblock copolymer," European Journal of Pharmaceutical Sciences, vol. 23, pp. 245-251 (2004). (Month not cited on publication).
Koster et al., "Drop-based microfluidic devices for encapsulation of single cells", Lab on a Chip The Royal Soc. of Chem. 8:1110-1115 (2008). (Month not cited on publication).
Li, Y., et al., "PEGylated PLGA nanoparticles as protein carriers: synthesis, preparation and biodistribution in rats," Journal of Controlled Release, vol. 71, pp. 203-211 (2001). (Month not cited on publication).
Loscertales, Micro/Nano encapsulation via electrified coaxial liquid jets. Science. 2002;295:1695-98. (Mar. 2002).
Love, A microengraving method for rapid selection of single cells producing antigen-specific antibodies. Nature Biotech. Jun. 2006:24(6):703-07.
Mazutis et al., Selective droplet coalescence using microfluidic systems. Lab Chip. Apr. 24, 2012; 12(10):1800-6.
Mirzabekov, "DNA Sequencing by Hybridization—a Megasequencing Method and a Diagnostic Tool?" Trends in Biotechnology 12(1): 27-32 (1994) (Jan. 1994).
Mouritzen et al., Single nucleotide polymorphism genotyping using locked nucleic acid (LNA). Expert Rev Mol Diagn. Jan. 2003;3(1):27-38.
Nguyen, "In situ hybridization to chromosomes stabilized in gel microdrops", Cytometry, 21:111-119 (1995). (Month not cited on publication).
Nisisako et al., Formation of droplets using branch channels in a microfluidic circuit. SICE. Osaka. Aug. 5-7, 2002. 957-959.
Okushima, "Controlled production of monodisperse double emulsions by two-step droplet breakup in microfluidic devices", Langmuir, 20:9905-9908 (2004). (Month not cited on publication).
Perez, C., et al., "Poly(lactic acid)-poly(ethylene glycol) nanoparticles as new carriers for the delivery of plasmid DNA," Journal of Controlled Release, vol. 75, pp. 211-224 (2001). (Month not cited on publication).
Ryan, "Rapid assay for mycobacterial growth and antibiotic susceptibility using gel microdrop and encapsulation", J. Clinical Microbiol., 33:7 1720-1726 (1995). (Jul. 1995).
Schirinzi et al., Combinatorial sequencing-by-hybridization: analysis of the NF1 gene. Genet Test. 2006 Spring;10(1):8-17. (Month not cited on publication).
Schmitt, "Bead-based multiplex genotyping of human papillomaviruses", J. Clinical Microbiol., 44:2 504-512 (2006). (Feb. 2006).
Shah, "Fabrication of monodisperse thermosensitive microgels and gel capsules in microfluidic devices", Soft Matter, 4:2303-2309 (2008). (Month not cited on publication).
Simeonov et al., Single nucleotide polymorphism genotyping using short, fluorescently labeled locked nucleic acid (LNA) probes and fluorescence polarization detection. Nucleic Acids Res. Sep. 1, 2002;30(17):e91.
Sorokin et al., Discrimination between perfect and mismatched duplexes with oligonucleotide gel microchips: role of thermodynamic and kinetic effects during hybridization. J Biomol Struct Dyn. Jun. 2005;22(6):725-34.
Su et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).
Sun et al., Progress in research and application of liquid-phase chip technology. Chinese Journal Experimental Surgery. May 2005;22(5):639-40.
Taniguchi et al., Chemical reactions in microdroplets by electrostatic manipulation of droplets in liquid media. Lab Chip. Feb. 2002;2(1):19-23. DOI: 10.1039/B108739H.
Tawfik, et al. Man-made cell-like compartments for molecular evolution. Nat Biotechnol. Jul. 1998;16(7):652-6.
Thorsen, et al. Dynamic pattern formation in a vesicle-generating microfluidic device. Physical Review Letters. American Physical Society. 2001; 86(18):4163-4166.
Umbanhowar, et al. Monodisperse emulsion generation via drop break off in a coflowing stream. Langmuir. 2000; 16:347-351.
Van De Hulst et al., Glare points. Appl Opt. Nov. 20, 1991;30(33):4755-63.
Wang et al., Single nucleotide polymorphism discrimination assisted by improved base stacking hybridization using oligonucleotide microarrays. Biotechniques. 2003;35:300-08. (Aug. 2003).
Weaver, "Rapid clonal growth measurements at the single-cell level: gel microdroplets and flow cytometry", Biotechnology, 9:873-877 (1991). (Sep. 1991).
Whitesides, "Soft lithography in biology and biochemistry", Annual Review of Biomedical Engineering, 3:335-373 (2001). (Month not cited on publication).
Xia, "Soft lithography", Annual Review of Material Science, 28:153-184 (1998). (Month not cited on publication).
Zhang, "Combinatorial marking of cells and organelles with reconstituted fluorescent proteins", Cell, 119:137-144 (Oct. 1, 2004).
Zhao, J., et al., "Preparation of hemoglobin-loaded nano-sized particles with porous structure as oxygen carriers," Biomaterials, vol. 28, pp. 1414-1422 (2007). Available online Nov. 2006.
Zimmerman, Microscale production of hybridomas by hypo-osmolar electrofusion. Hum Antibod Hybridomas. 1992;3 (January):14-18.
Extended European Search Report dated Jan. 19, 2018 for Application No. EP 16197694.9.
U.S. Appl. No. 15/670,977, filed Aug. 7, 2017, Weitz et al.
U.S. Appl. No. 15/792,218, filed Oct. 24, 2017, Weitz et al.
U.S. Appl. No. 15/670,885, filed Aug. 7, 2017, Weitz et al.
U.S. Appl. No. 15/427,511, filed Feb. 8, 2017, Weitz et al.
EP 17194710.4, Jan. 19, 2018, Extended European Search Report.

ASSAYS AND OTHER REACTIONS INVOLVING DROPLETS

RELATED APPLICATIONS

This application is a continuation of U.S. patent application Ser. No. 15/670,977, filed Aug. 7, 2017 which is a continuation of U.S. patent application Ser. No. 15/449,637, filed Mar. 3, 2017, which is a continuation of U.S. patent application Ser. No. 14/721,558, filed May 26, 2015, which is a continuation of U.S. patent application Ser. No. 14/172,326, filed Feb. 4, 2014, which is a continuation of U.S. patent application Ser. No. 12/529,926, with a § 371 date of Feb. 10, 2010, which is a national stage filing under 35 U.S.C. § 371 of Int. Patent Application Serial No. PCT/US2008/003185, filed Mar. 7, 2008, which claims the benefit of U.S. Provisional Patent Application Ser. No. 60/905,567, filed Mar. 7, 2007, the contents of each of which are incorporated herein by reference in their entities.

FIELD OF INVENTION

The present invention generally relates to droplets and/or emulsions. In some cases, the droplets and/or emulsions may be used in assays.

BACKGROUND

An emulsion is a fluidic state which exists when a first fluid is dispersed in a second fluid that is typically immiscible or substantially immiscible with the first fluid. Examples of common emulsions are oil in water and water in oil emulsions. Multiple emulsions are emulsions that are formed with more than two fluids, or two or more fluids arranged in a more complex manner than a typical two-fluid emulsion. For example, a multiple emulsion may be oil-in-water-in-oil, or water-in-oil-in-water. Multiple emulsions are of particular interest because of current and potential applications in fields such as pharmaceutical delivery, paints and coatings, food and beverage, and health and beauty aids.

Typically, multiple emulsions consisting of a droplet inside another droplet are made using a two-stage emulsification technique, such as by applying shear forces through mixing to reduce the size of droplets formed during the emulsification process. Other methods such as membrane emulsification techniques using, for example, a porous glass membrane, have also been used to produce water-in-oil-in-water emulsions. Microfluidic techniques have also been used to produce droplets inside of droplets using a procedure including two or more steps. For example, see International Patent Application No. PCT/US2004/010903, filed Apr. 9, 2004, entitled "Formation and Control of Fluidic Species," by Link, et al., published as WO 2004/091763 on Oct. 28, 2004; or International Patent Application No. PCT/US03/20542, filed Jun. 30, 2003, entitled "Method and Apparatus for Fluid Dispersion," by Stone, et al., published as WO 2004/002627 on Jan. 8, 2004, each of which is incorporated herein by reference. See also Anna, et al., "Formation of Dispersions using 'Flow Focusing' in Microchannels," *Appl. Phys. Lett.,* 82:364 (2003) and Okushima, et al., "Controlled Production of Monodispersed Emulsions by Two-Step Droplet Breakup in Microfluidic Devices," *Langmuir* 20:9905-9908 (2004). In some of these examples, a T-shaped junction in a microfluidic device is used to first form an aqueous droplet in an oil phase, which is then carried downstream to another T-junction where the aqueous droplet contained in the oil phase is introduced into another aqueous phase. In another technique, co-axial jets can be used to produce coated droplets, but these coated droplets must be re-emulsified into the continuous phase in order to form a multiple emulsion. See Loscertales et al., "Micro/Nano Encapsulation via Electrified Coaxial Liquid Jets," *Science* 295:1695 (2002).

Multiple emulsions and the products that can be made from them can be used to produce a variety of products useful in the food, coatings, cosmetic, or pharmaceutical industries, for example. Methods for producing multiple emulsions providing consistent droplet sizes, consistent droplet counts, consistent coating thicknesses, and/or improved control would make commercial implementation of these products more viable.

SUMMARY OF THE INVENTION

The present invention generally relates to droplets and/or emulsions. In some cases, the droplets and/or emulsions may be used in assays. The subject matter of the present invention involves, in some cases, interrelated products, alternative solutions to a particular problem, and/or a plurality of different uses of one or more systems and/or articles.

In one aspect, the invention is a method. In one set of embodiments, the method includes acts of providing a fluidic droplet containing a species, hardening the fluidic droplet containing the species, and exposing the species within the hardened fluidic droplet to a reactant. In another set of embodiments, the method includes acts of providing a gel droplet comprising a first nucleic acid and a second nucleic acid different from the first nucleic acid, the first nucleic acid being bound to the gel, and growing the first nucleic acid within the gel, using the second nucleic acid as a template. In still another set of embodiments, the method includes acts of providing a fluidic droplet containing a species, hardening the fluidic droplet containing the species, and liquefying the hardened fluidic droplet. In another set of embodiments, the method includes acts of providing a first fluidic droplet and a second fluidic droplet, and causing the first fluidic droplet and the second fluidic droplet to fuse, wherein the fused droplet hardens.

The method, in yet another set of embodiments, includes hardening a fluidic droplet containing cells, and causing the cells within the hardened fluidic droplet to multiply.

In another set of embodiments, the method includes an act of causing a PCR reaction to occur within a gel droplet. In still another set of embodiments, the method includes an act of forming a gel droplet containing a PCR primer bound to the gel.

In one set of embodiments, the method includes acts of providing a fluidic droplet in a carrying fluid, the fluidic droplet substantially immiscible in water and the carrying fluid substantially immiscible in water, hardening the fluidic droplet, removing the carrying fluid, and placing the hardened fluidic droplet in a third fluid.

In another aspect, the invention is an article. In one embodiment, the article includes a gel droplet containing a clonal population of cells.

In another embodiment, the article includes a gel droplet containing a PCR primer bound to the gel.

In another aspect, the present invention is directed to a method of making one or more of the embodiments described herein. In another aspect, the present invention is directed to a method of using one or more of the embodiments described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
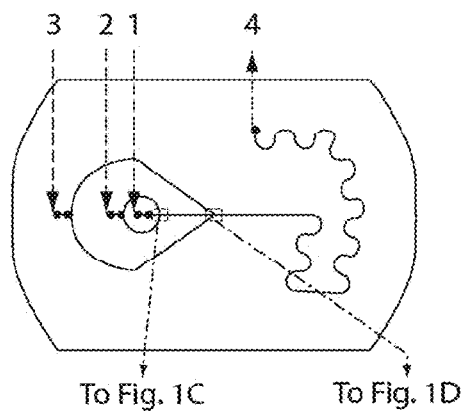
FIGS. 1A-1D illustrates a microfluidic device of one embodiment of the invention.

The present invention generally relates to droplets and/or emulsions, such as multiple emulsions. In some cases, the droplets and/or emulsions may be used in assays, and in certain embodiments, the droplet or emulsion may be hardened to form a gel. In some aspects, a heterogeneous assay can be performed using the gel. For example, a droplet may be hardened to form a gel, where the droplet contains a cell, DNA, or other suitable species. The gel may be exposed to a reactant, and the reactant may interact with the gel and/or with the cell, DNA, etc., in some fashion. For example, the reactant may diffuse through the gel, or the hardened particle (or a portion thereof) may liquefy to form a liquid state, allowing the reactant to interact with the cell. As a specific example, DNA contained within a gel particle may be subjected to PCR (polymerase chain reaction) amplification, e.g., by using PCR primers able to bind to the gel as it forms. As the DNA is amplified using PCR, some of the DNA will be bound to the gel via the PCR primer. After the PCR reaction, unbound DNA may be removed from the gel, e.g., via diffusion or washing. Thus, a gel particle having bound DNA may be formed in one embodiment of the invention.

Thus, in one aspect, the invention involves reactions involving liquid droplets, for example, droplets contained within emulsions such as multiple emulsions. In certain embodiments, systems and methods are providing for causing two or more droplets to fuse or coalesce, e.g., in cases where the droplets ordinarily are unable to fuse or coalesce, for example due to composition, surface tension, size, etc., e.g., to cause a reaction to occur. For example, in a microfluidic system, the surface tension of the fluidic droplets, relative to their size, may prevent fusion of the fluidic droplets. The fluidic droplets may each independently contain gas or liquid.

Fields in which droplets and emulsions may prove useful include, for example, food, beverage, health and beauty aids, paints and coatings, and drugs and drug delivery. For instance, a precise quantity of a drug, pharmaceutical, or other agent can be encapsulated by a shell designed to release its contents under particular conditions, as described in detail below. In some instances, cells can be contained within a droplet, and the cells can be stored and/or delivered. Other species that can be stored and/or delivered include, for example, biochemical species such as nucleic acids such as siRNA, RNAi and DNA, proteins, peptides, or enzymes. Additional species that can be incorporated within a droplet or emulsion of the invention include, but are not limited to, nanoparticles, quantum dots, fragrances, proteins, indicators, dyes, fluorescent species, chemicals, or the like. A droplet or emulsion can also serve as a reaction vessel in certain cases, such as for controlling chemical reactions, or for in vitro transcription and translation, e.g., for directed evolution technology.

Using the methods and devices described herein, in some embodiments, a consistent size and/or number of droplets can be produced, and/or a consistent ratio of size and/or number of outer droplets to inner droplets, inner droplets to other inner droplets, or other such ratios, can be produced. For example, in some cases, a single droplet within an outer droplet of predictable size can be used to provide a specific quantity of a drug. In addition, combinations of compounds or drugs may be stored, transported, or delivered in a emulsion or droplet. For instance, hydrophobic and hydrophilic species can be delivered in a single droplet, as the droplet can include both hydrophilic and hydrophobic portions. The amount and concentration of each of these portions can be consistently controlled according to certain embodiments of the invention, which can provide for a predictable and consistent ratio of two or more species in the multiple droplet.

Thus, in one aspect, the present invention is directed to systems, assays, methods, etc. involving gels produced as described herein, e.g., gel particles, gel capsules, and the like. In some cases, a heterogeneous assay involving the gel can be performed. A gel may allow easier use of a heterogeneous assay than by using a liquid emulsion drop directly. That is, once a gel is formed, its composition can be changed by adding new reagents or washing out old ones.

One non-limiting example of a heterogeneous assay in a microgel particle is similar to a "polony," as described in detail in U.S. Pat. Nos. 6,432,360, 6,485,944 and 6,511,803, and in PCT/US05/06425, each incorporated by reference, as well as U.S. patent application Ser. No. 11/505,073, also incorporated herein by reference. Briefly, in one embodiment, one or more DNA molecules (or other species, as described herein), either naked, or contained within an intact cell, are encapsulated within a microgel at the time of formation, e.g., by forming a droplet containing the cell, DNA molecule, other species, etc., then hardening the droplet, e.g., to form a gel. In some cases, molecules of one or more PCR primers having 5' acrydite moieties may be included in the droplet, prior to hardening. Upon polymerization of the gel, the primer may be covalently coupled to the gel matrix, via the acrydite. The emulsion droplets may thus be collected and caused to polymerize or gel. The surrounding fluid (e.g., an oil phase) can then be removed, e.g., by washing away with a suitable solvent, leaving gel particles containing the cell, DNA molecule, other species, etc., and the PCR primers. The gels can, in some cases, be resuspended in an aqueous solution containing reagents for PCR (e.g., buffering components, salts, dNTPs, DNA polymerase, and/or one or more PCR primers with no acrydite modification). The suspension of gel particles can then be thermally cycled in a test tube, e.g., using standard PCR cycling techniques known to those of ordinary skill in the art, which may allow PCR amplification to occur, e.g., between pairs of primers. The strand of DNA synthesized from the acrydite-modified primers may thus be covalently coupled to the gel in some cases.

The gels can be washed to remove unreacted or unbound PCR components, including DNA strands synthesized from non-acrydite primers. The remaining covalently attached DNA strand can be probed using techniques known to those of ordinary skill in the art, for example, by binding sequence-specific fluorescent oligonucleotides and washing away unbound probes. As another example, a single-base extension reaction can be used to probe the DNA sequence at a particular site. The fluorescence of the gel from the bound oligonucleotides can be measured by measured using techniques known to those of ordinary skill in the art, such as fluorescence microscopy or by FACS. Either the presence or absence of a sequence can be determined, and/or the sequence state at one or more positions can be determined, for example, genotyping by SNPs. For instance, by using FACS, sub-populations of the gels can be sorted and analyzed separately.

As discussed herein, in another set of embodiments, cells of any type (prokaryotic or eukaryotic) can be encapsulated in the gel, and the DNA or RNA within the cell can be used as a template for enzymatic amplification, in one embodiment of the invention. This could be done, for example, by reverse transcription PCR (rtPCR) for the study of RNA within the cell, or standard PCR for DNA. As another example, other types of enzymatic amplification, such as whole-genome amplification by phi29 polymerase, can also be performed.

As yet another example, a collection of gels with covalently attached DNA may be used as a library, e.g., that could be probed and washed many times in succession, which would be especially useful when whole genomes are amplified in the gel, since many regions of the DNA could be probed over time. Furthermore, in some cases, by doing PCR from the library gels using unmodified primers, chosen sections of DNA can be amplified away from the gel and analyzed further. For example, a gene can be amplified from a sub-population of library gels and then the supernatant from the PCR could be sequenced by standard methods.

In another embodiment of the invention, particles, such as polymer beads, may be encapsulated or incorporated into droplets which are then hardened into gels (e.g., forming gel particles, gel capsules, etc.). In one embodiment, the beads may be magnetic, which could allow for the magnetic manipulation of the gels. The beads could also be functionalized so that they could have other molecules attached, such as proteins, nucleic acids or small molecules. One embodiment of the present invention is directed to a set of beads encoding a library of, for example, nucleic acids, proteins, small molecules, or other species as described herein, that would stay embedded in a gel particle indefinitely.

As mentioned, in certain aspects, the invention generally relates to emulsions and/or droplets. The emulsion may include droplets, such as those described above, and/or colloid particles. As used herein, an "emulsion" is given its ordinary meaning as used in the art, i.e., a liquid dispersion. In some cases, the emulsion may be a "microemulsion" or a "nanoemulsion," i.e., an emulsion having a dispersant on the order of microns or nanometers, respectively. The dispersion or emulsion, in some cases, may include droplets having a homogenous distribution of diameters, i.e., the droplets may have a distribution of diameters such that no more than about 10%, about 5%, about 3%, about 1%, about 0.03%, or about 0.01% of the droplets have an average diameter greater than about 10%, about 5%, about 3%, about 1%, about 0.03%, or about 0.01% of the average diameter of the droplets. As one example, such an emulsion may be created by allowing fluidic droplets of the appropriate size or sizes (e.g., created as described herein) to enter into a solution that is immiscible with the fluidic droplets.

Techniques for forming droplets have been disclosed in, for example, U.S. patent application Ser. No. 11/360,845, filed Feb. 23, 2006, entitled "Electronic Control of Fluidic Species," by Link, et al., published as U.S. Patent Application Publication No. 2007/000342 on Jan. 4, 2007, incorporated herein by reference. For example, electric fields may be used to create droplets of fluid surrounded by a liquid. The fluid and the liquid may be essentially immiscible in many cases, i.e., immiscible on a time scale of interest (e.g., the time it takes a fluidic droplet to be transported through a particular system or device). In certain cases, the droplets may each be substantially the same shape or size, as further described below. The fluid may also contain other species, for example, certain molecular species (e.g., as further discussed below), cells, particles, etc.

The electric field, in some embodiments, is generated from an electric field generator, i.e., a device or system able to create an electric field that can be applied to the fluid. The electric field generator may produce an AC field (i.e., one that varies periodically with respect to time, for example, sinusoidally, sawtooth, square, etc.), a DC field (i.e., one that is constant with respect to time), a pulsed field, etc. The electric field generator may be constructed and arranged to create an electric field within a fluid contained within a channel or a microfluidic channel. The electric field generator may be integral to or separate from the fluidic system containing the channel or microfluidic channel, according to some embodiments. As used herein, "integral" means that portions of the components integral to each other are joined in such a way that the components cannot be manually separated from each other without cutting or breaking at least one of the components.

Techniques for producing a suitable electric field (which may be AC, DC, etc.) are known to those of ordinary skill in the art. For example, in one embodiment, an electric field is produced by applying voltage across a pair of electrodes, which may be positioned on or embedded within the fluidic system (for example, within a substrate defining the channel or microfluidic channel), and/or positioned proximate the fluid such that at least a portion of the electric field interacts with the fluid. The electrodes can be fashioned from any suitable electrode material or materials known to those of ordinary skill in the art, including, but not limited to, silver, gold, copper, carbon, platinum, copper, tungsten, tin, cadmium, nickel, indium tin oxide ("ITO"), etc., as well as combinations thereof. In some cases, transparent or substantially transparent electrodes can be used.

In some embodiments of the invention, systems and methods are provided for at least partially neutralizing an electric charge present on a fluidic droplet, for example, a fluidic droplet having an electric charge, as described above. For example, to at least partially neutralize the electric charge, the fluidic droplet may be passed through an electric field and/or brought near an electrode, e.g., using techniques such as those described herein. Upon exiting of the fluidic droplet from the electric field (i.e., such that the electric field no longer has a strength able to substantially affect the fluidic droplet), and/or other elimination of the electric field, the fluidic droplet may become electrically neutralized, and/or have a reduced electric charge.

In another set of embodiments, droplets of fluid can be created from a fluid surrounded by a liquid within a channel by altering the channel dimensions in a manner that is able to induce the fluid to form individual droplets. The channel may, for example, be a channel that expands relative to the direction of flow, e.g., such that the fluid does not adhere to the channel walls and forms individual droplets instead, or a channel that narrows relative to the direction of flow, e.g., such that the fluid is forced to coalesce into individual droplets. In other embodiments, internal obstructions may also be used to cause droplet formation to occur. For instance, baffles, ridges, posts, or the like may be used to disrupt liquid flow in a manner that causes the fluid to coalesce into fluidic droplets.

In some cases, the channel dimensions may be altered with respect to time (for example, mechanically or electromechanically, pneumatically, etc.) in such a manner as to cause the formation of individual fluidic droplets to occur. For example, the channel may be mechanically contracted ("squeezed") to cause droplet formation, or a fluid stream may be mechanically disrupted to cause droplet formation, for example, through the use of moving baffles, rotating blades, or the like.

In some cases, an emulsion may include a larger fluidic droplet that contains one or more smaller droplets therein which, in some cases, can contain even smaller droplets therein, etc. In some cases, the droplet is surrounded by a liquid (e.g., suspended). Any of these droplets may be of substantially the same shape and/or size (i.e., "monodisperse"), or of different shapes and/or sizes, depending on the particular application. As used herein, the term "fluid" generally refers to a substance that tends to flow and to conform to the outline of its container, i.e., a liquid, a gas, a viscoelastic fluid, etc. Typically, fluids are materials that are unable to withstand a static shear stress, and when a shear stress is applied, the fluid experiences a continuing and permanent distortion.

The fluid may have any suitable viscosity that permits flow, for example, a viscosity similar to water (e.g., as in an aqueous solution), oil, etc. In certain embodiments of the invention, the liquid may include an oil or an organic solvent, such as those known to ordinary skill in the art. If two or more fluids are present, each fluid may be independently selected among essentially any fluids (liquids, gases, and the like) by those of ordinary skill in the art, by considering the relationship between the fluids. The fluids may each be miscible or immiscible. For example, two fluids can be selected to be immiscible within the time frame of formation of a stream of fluids, or within the time frame of reaction or interaction. As an example, where the portions remain liquid for a significant period of time, the fluids may be immiscible. As another example, where, after contact and/or formation, the dispersed portions are quickly hardened by polymerization or the like, the fluids need not be as immiscible. Those of ordinary skill in the art can select suitable miscible or immiscible fluids, using contact angle measurements or the like, to carry out the techniques of the invention.

A "droplet," as used herein, is an isolated portion of a first fluid that is surrounded by a second fluid. It is to be noted that a droplet is not necessarily spherical, but may assume other shapes as well, for example, depending on the external environment. In one embodiment, the droplet has a minimum cross-sectional dimension that is substantially equal to the largest dimension of the channel perpendicular to fluid flow in which the droplet is located.

As used herein, a first entity is "surrounded" by a second entity if a closed loop can be drawn around the first entity through only the second entity. A first entity is "completely surrounded" if closed loops going through only the second entity can be drawn around the first entity regardless of direction. In one aspect, the first entity may be a cell, for example, a cell suspended in media is surrounded by the media. In another aspect, the first entity is a particle. In yet another aspect of the invention, the entities can both be fluids. For example, a hydrophilic liquid may be suspended in a hydrophobic liquid, a hydrophobic liquid may be suspended in a hydrophilic liquid, a gas bubble may be suspended in a liquid, etc. Typically, a hydrophobic liquid and a hydrophilic liquid are substantially immiscible with respect to each other, where the hydrophilic liquid has a greater affinity to water than does the hydrophobic liquid. Examples of hydrophilic liquids include, but are not limited to, water and other aqueous solutions comprising water, such as cell or biological media, ethanol, salt solutions, etc. Examples of hydrophobic liquids include, but are not limited to, oils such as hydrocarbons, silicon oils, fluorocarbon oils, organic solvents etc.

Many such oils are commercially available. As discussed above, the oil may be chosen so as to be substantially immiscible in water, for instance, with solubilities of less than about 50 ppb, less than about 25 ppb, or less than about 10 ppb (without surfactant). Examples of potentially suitable hydrocarbons include, but are not limited to, light mineral oil (Sigma), kerosene (Fluka), hexadecane (Sigma), decane (Sigma), undecane (Sigma), dodecane (Sigma), octane (Sigma), cyclohexane (Sigma), hexane (Sigma), or the like. Non-limiting examples of potentially suitable silicone oils include 2 cst polydimethylsiloxane oil (Sigma). Non-limiting examples of fluorocarbon oils include FC3283 (3M), FC40 (3M), Krytox GPL (Dupont), etc. In some cases, oils potentially suitable for the invention include those that have viscosities of between about 0.8 cSt and about 1 cSt, or between about 0.7 cSt and about 0.9 cSt. In certain embodiments, the oil may have a specific gravity of between about 1.4 and about 2, or between about 1.6 and about 1.7 at 25° C., and/or a specific gravity of between about 1.2 and about 1.8, or between about 1.4 and about 1.5 at 100° C. The oil may also have a boiling point of greater than about 100° C., or greater than about 120° C. in some cases. In one set of embodiments, the oil may be chosen so as to have an interfacial tension with phosphate-buffered saline of between about 60 mN/m and about 70 mN/m, e.g., about 63 mN/m. In some cases, a surfactant may also be present, as is discussed below. Non-limiting examples of surfactants potentially useful in the invention include Span80 (Sigma), Span80/Tween-20 (Sigma), Span80/Triton X-100 (Sigma), Abil EM90 (Degussa), Abil we09 (Degussa), polyglycerol polyricinoleate "PGPR90" (Danisco), Tween-85, 749 Fluid (Dow Corning), the ammonium carboxylate salt of Krytox 157 FSL (Dupont), the ammonium carboxylate salt of Krytox 157 FSM (Dupont), or the ammonium carboxylate salt of Krytox 157 FSH (Dupont).

The "cross-sectional dimension" of the channel is measured perpendicular to the direction of fluid flow. Most fluid channels in components of the invention have maximum cross-sectional dimensions less than 2 mm, and in some cases, less than 1 mm. In one set of embodiments, all fluid channels containing embodiments of the invention are microfluidic or have a largest cross sectional dimension of no more than 2 mm or 1 mm. In another embodiment, the fluid channels may be formed in part by a single component (e.g. an etched substrate or molded unit). Of course, larger channels, tubes, chambers, reservoirs, etc. can be used to store fluids in bulk and to deliver fluids to components of the invention. In one set of embodiments, the maximum cross-sectional dimension of the channel(s) containing embodiments of the invention are less than 500 microns, less than 200 microns, less than 100 microns, less than 50 microns, or less than 25 microns.

The fluidic droplets within the channels may have a cross-sectional dimension smaller than about 90% of an average cross-sectional dimension of the channel, and in certain embodiments, smaller than about 80%, about 70%, about 60%, about 50%, about 40%, about 30%, about 20%, about 10%, about 5%, about 3%, about 1%, about 0.5%, about 0.3%, about 0.1%, about 0.05%, about 0.03%, or about 0.01% of the average cross-sectional dimension of the channel.

In certain instances, the droplets may be contained within a carrying fluid, e.g., within a fluidic stream. The fluidic stream, in one set of embodiments, is created using a microfluidic system, discussed in detail below. In some cases, the droplets will have a homogenous distribution of diameters, i.e., the droplets may have a distribution of diameters such that no more than about 10%, about 5%, about 3%, about 1%, about 0.03%, or about 0.01% of the droplets have an average diameter greater than about 10%, about 5%, about 3%, about 1%, about 0.03%, or about 0.01% of the average diameter of the droplets. Techniques for producing such a homogenous distribution of diameters are disclosed in International Patent Application No. PCT/US2004/010903, filed Apr. 9, 2004, entitled "Formation and Control of Fluidic Species," by Link, et al., published as WO 2004/091763 on Oct. 28, 2004, incorporated herein by reference, and in other references as described below.

The fluidic droplets may each be substantially the same shape and/or size. Typically, monodisperse droplets are of substantially the same size. The shape and/or size of the fluidic droplets can be determined, for example, by measuring the average diameter or other characteristic dimension of the droplets. The "average diameter" of a plurality or series of droplets is the arithmetic average of the average diameters of each of the droplets. Those of ordinary skill in the art will be able to determine the average diameter (or other characteristic dimension) of a plurality or series of droplets, for example, using laser light scattering, microscopic examination, or other known techniques. The average diameter of a single droplet, in a non-spherical droplet, is the diameter of a perfect sphere having the same volume as the non-spherical droplet. The average diameter of a droplet (and/or of a plurality or series of droplets) may be, for example, less than about 1 mm, less than about 500 micrometers, less than about 200 micrometers, less than about 100 micrometers, less than about 17 micrometers, less than about 50 micrometers, less than about 25 micrometers, less than about 10 micrometers, or less than about 5 micrometers in some cases. The average diameter may also be at least about 1 micrometer, at least about 2 micrometers, at least about 3 micrometers, at least about 5 micrometers, at least about 10 micrometers, at least about 15 micrometers, or at least about 20 micrometers in certain cases.

The term "determining," as used herein, generally refers to the analysis or measurement of a species, for example, quantitatively or qualitatively, and/or the detection of the presence or absence of the species. "Determining" may also refer to the analysis or measurement of an interaction between two or more species, for example, quantitatively or qualitatively, or by detecting the presence or absence of the interaction. Examples of suitable techniques include, but are not limited to, spectroscopy such as infrared, absorption, fluorescence, UV/visible, FTIR ("Fourier Transform Infrared Spectroscopy"), or Raman; gravimetric techniques; ellipsometry; piezoelectric measurements; immunoassays; electrochemical measurements; optical measurements such as optical density measurements; circular dichroism; light scattering measurements such as quasielectric light scattering; polarimetry; refractometry; or turbidity measurements.

In some cases, a plurality of droplets may be substantially the same. It should be understood that, even if the droplets appear to be substantially identical, or to contain substantially the same number of droplets therein, not all of the droplets will necessarily be completely identical. In some cases, there may be minor variations in the number and/or size of droplets contained within a surrounding droplet. Thus, in some cases, at least about 17%, at least about 80%, at least about 85%, at least about 90%, at least about 92%, at least about 94%, at least about 95%, at least about 96%, at least about 97%, at least about 98%, or at least about 99% of a plurality of outer droplets may each contain the same number of inner fluidic droplets therein.

As used herein, the term "fluid stream" or "fluidic stream" refers to the flow of a fluid, typically generally in a specific direction. The fluidic stream may be continuous and/or discontinuous. A "continuous" fluidic stream is a fluidic stream that is produced as a single entity, e.g., if a continuous fluidic stream is produced from a channel, the fluidic stream, after production, appears to be contiguous with the channel outlet. The continuous fluidic stream may be laminar, or turbulent in some cases. The continuous fluidic stream may be, e.g., solid or hollow (i.e., containing a second fluid internally, for example, as in a hollow tube). It is to be understood that wherever "tube" is used herein, the structure can be a hollow, a solid or filled (i.e., not hollow) stream, a stream that includes a central core and a surrounding layer or layers, any of which can be selectively reacted with any others, or solidified, or the like. In some cases, the central core is hollow, and/or fluid may be removed from a hardened surrounding fluid to produce a hollow tube.

Similarly, a "discontinuous" fluidic stream is a fluidic stream that is not produced as a single entity. A discontinuous fluidic stream may have the appearance of individual droplets, optionally surrounded by a second fluid. A "droplet," as used herein, is an isolated portion of a first fluid that completely surrounded by a second fluid. In some cases, the droplets may be spherical or substantially spherical; however, in other cases, the droplets may be non-spherical, for example, the droplets may have the appearance of "blobs" or other irregular shapes, for instance, depending on the external environment.

In another aspect, the methods and apparatus of the invention can be used to form droplets containing species and to provide methods of delivering such species. For example, in certain embodiments of the invention, the fluidic droplets may contain additional entities or species, for example, other chemical, biochemical, or biological entities (e.g., dissolved or suspended in the fluid), cells, particles, beads, gases, molecules, pharmaceutical agents, drugs, DNA, RNA, proteins, fragrance, reactive agents, biocides, fungicides, preservatives, chemicals, or the like. Cells, for example, can be suspended in a fluid multiple emulsion, or contained in a polymerosome. Thus, the species may be any substance that can be contained in any portion of a droplet and can be differentiated from the droplet fluid. The species may be present in any fluidic droplet, for example, within an inner droplet and/or within an outer droplet, etc. In some cases, the droplets may each be substantially the same shape or size, as discussed above. In certain embodiments, any of the droplets disclosed herein (e.g., a hardened droplet) may contain one or more species.

As the polydispersity and size of the droplets can be narrowly controlled, emulsions can be formed that include a specific number of species or particles per droplet. For instance, a single droplet may contain 1, 2, 3, 4, or more species. The emulsions can be formed with low polydispersity so that greater than 90%, 95%, or 99% of the droplets formed contain the same number of species. In certain instances, the invention provides for the production of droplets consisting essentially of a substantially uniform number of entities of a species therein (i.e., molecules, cells, particles, etc.). For example, at least about 17%, at least about 80%, at least about 85%, at least about 90%, at least about 92%, at least about 94%, at least about 95%, at least about 96%, at least about 97%, at least about 98%, or at least about 99%, or more of a plurality or series of droplets may each contain at least one entity, and/or may contain the same number of entities of a particular species. For instance, a substantial number of fluidic droplets produced, e.g., as described above, may each contain 1 entity, 2 entities, 3 entities, 4 entities, 5 entities, 7 entities, 10 entities, 15 entities, 20 entities, 25 entities, 30 entities, 40 entities, 50 entities, 60 entities, 70 entities, 80 entities, 90 entities, 100 entities, etc., where the entities are molecules or macromolecules, cells, particles, etc. In some cases, the droplets may each independently contain a range of entities, for example, less than 20 entities, less than 15 entities, less than 10 entities, less than 7 entities, less than 5 entities, or less than 3 entities in some cases.

In one set of embodiments, in a plurality of droplets of fluid, some of which contain a species of interest and some of which do not contain the species of interest, the droplets of fluid may be screened or sorted for those droplets of fluid containing the species, and in some cases, the droplets may be screened or sorted for those droplets of fluid containing a particular number or range of entities of the species of interest. Systems and methods for screening and/or sorting droplets are disclosed in, for example, U.S. patent application Ser. No. 11/360,845, filed Feb. 23, 2006, entitled "Electronic Control of Fluidic Species," by Link, et al., published as U.S. Patent Application Publication No. 2007/000342 on Jan. 4, 2007, incorporated herein by reference.

Thus, in some cases, a plurality or series of fluidic droplets, some of which contain the species and some of which do not, may be enriched (or depleted) in the ratio of droplets that do contain the species, for example, by a factor of at least about 2, at least about 3, at least about 5, at least about 10, at least about 15, at least about 20, at least about 50, at least about 100, at least about 125, at least about 150, at least about 200, at least about 250, at least about 500, at least about 170, at least about 1000, at least about 2000, or at least about 5000 or more in some cases. In other cases, the enrichment (or depletion) may be in a ratio of at least about $10^4$, at least about $10^5$, at least about $10^6$, at least about $10^7$, at least about $10^8$, at least about $10^9$, at least about $10^{10}$, at least about $10^{11}$, at least about $10^{12}$, at least about $10^{13}$, at least about $10^{14}$, at least about $10^{15}$, or more. For example, a fluidic droplet containing a particular species may be selected from a library of fluidic droplets containing various species, where the library may have about $10^5$, about $10^6$, about $10^7$, about $10^8$, about $10^9$, about $10^{10}$, about $10^{11}$, about $10^{12}$, about $10^{13}$, about $10^{14}$, about $10^{15}$, or more items, for example, a DNA library, an RNA library, a protein library, a combinatorial chemistry library, etc. In certain embodiments, the droplets carrying the species may then be fused, reacted, or otherwise used or processed, etc., as further described herein, for example, to initiate or determine a reaction.

In one set of embodiments, the fluidic droplets may contain cells or other entities, such as proteins, viruses, macromolecules, particles, etc. As used herein, a "cell" is given its ordinary meaning as used in biology. One or more cells and/or one or more cell types can be contained in a droplet. The inner fluid may be, for example, an aqueous buffer solution. The cell may be any cell or cell type. For example, the cell may be a bacterium or other single-cell organism, a plant cell, or an animal cell. If the cell is a single-cell organism, then the cell may be, for example, a protozoan, a trypanosome, an amoeba, a yeast cell, algae, etc. If the cell is an animal cell, the cell may be, for example, an invertebrate cell (e.g., a cell from a fruit fly), a fish cell (e.g., a zebrafish cell), an amphibian cell (e.g., a frog cell), a reptile cell, a bird cell, or a mammalian cell such as a primate cell, a bovine cell, a horse cell, a porcine cell, a goat cell, a dog cell, a cat cell, or a cell from a rodent such as a rat or a mouse. If the cell is from a multicellular organism, the cell may be from any part of the organism. For instance, if the cell is from an animal, the cell may be a cardiac cell, a fibroblast, a keratinocyte, a heptaocyte, a chondracyte, a neural cell, a osteocyte, a muscle cell, a blood cell, an endothelial cell, an immune cell (e.g., a T-cell, a B-cell, a macrophage, a neutrophil, a basophil, a mast cell, an eosinophil), a stem cell, etc. In some cases, the cell may be a genetically engineered cell. In certain embodiments, the cell may be a Chinese hamster ovarian ("CHO") cell or a 3T3 cell.

For example, an emulsion can be formed in which greater than about 95% of the droplets formed contain a single cell at the point of droplet production, without a need to separate or otherwise purify the emulsion in order to obtain this level of dispersity. Typically, the fluid supporting the cell is the innermost fluid and is aqueous based. The surrounding fluid may be a non-aqueous fluid and other fluids, e.g., within a multiple emulsion, may be aqueous or non-aqueous. If a polymerosome is used, the shell surrounding the cell (which may or may not be the outermost fluidic droplet in a multiple emulsion) may be formed of a material capable of protecting the cell. The shell may help retain, for example, moisture, and can be sized appropriately to maximize the lifetime of the cell within the polymerosome. For instance, the shell may be sized to contain a specific volume, e.g., 10 nL, of inner fluid as well as a single cell or a select number of cells. Likewise, cells may be suspended so that, statistically, one cell will be included with each aliquot (e.g., 10 nL) of fluid within a droplet.

In one set of embodiments, a fluidic droplet of the present invention, or a portion thereof, may be hardened into a solid. As used herein, the "hardening" of a fluidic stream refers to a process by which at least a portion of the fluidic stream is converted into a solid or at least a semi-solid state (e.g., a gel, a viscoelastic solid, etc.). In some embodiments of the invention, a droplet may be hardened, such as by using a fluid that can be solidified, gelled, and/or polymerized (e.g., to form a polymerosome). The droplet may be an outer droplet or one contained within a surrounding droplet. In some cases, capsules or spheres can be formed, i.e., by hardening a droplet containing one or more fluidic droplets therein. For example, a solid sphere may be formed if an inner droplet is hardened, e.g., to form a gel. Any technique able to solidify a fluidic droplet can be used. For example, a fluidic droplet may be cooled to a temperature below the melting point or glass transition temperature of a fluid within the fluidic droplet, a chemical reaction may be induced that causes the fluidic droplet to solidify (for example, a polymerization reaction, a reaction between two fluids that produces a solid product, etc.), or the like. In some cases, the hardened droplet may contain an entity or species, as described above. For example, a droplet containing a cell may be hardened to form a gel. As another example, a droplet of an outer fluid, containing an inner fluid containing a cell, may be hardened to produce a gel "capsule" surrounding the inner fluid and the cell. In some cases, a probiotic may be incorporated or encapsulated within a gel or other hardened particle as a way to increase stability.

In some embodiments of the invention, a hardened shell may be formed around an inner droplet, such as by using a middle fluid that can be solidified or gelled. In this way, capsules can be formed with consistently and repeatedly-sized inner droplets, as well as a consistent and repeatedly-sized outer shell. In some embodiments, this can be accomplished by a phase change in the middle fluid.

In one embodiment, the fluidic droplet is solidified by reducing the temperature of the fluidic droplet to a temperature that causes at least one of the components of the fluidic droplet to reach a solid state. For example, the fluidic droplet may be solidified by cooling the fluidic droplet to a temperature that is below the melting point or glass transition temperature of a component of the fluidic droplet, thereby causing the fluidic droplet to become solid. As non-limiting examples, the fluidic droplet may be formed at an elevated temperature (i.e., above room temperature, about 25° C.), then cooled, e.g., to room temperature or to a temperature below room temperature; the fluidic droplet may be formed at room temperature, then cooled to a temperature below room temperature, or the like. As a specific example, a fluidic droplet may contain a gel such as a hydrogel, and the droplet may be solidified by cooling the droplet below its gelation temperature.

In some embodiments, this can be accomplished by a phase change in a fluid forming the droplet. A phase change can be initiated by a temperature change, for instance, and in some cases the phase change is reversible. For example, a wax or gel may be used as a fluid at a temperature which maintains the wax or gel as a fluid. Upon cooling, the wax or gel can form a solid or semisolid shell, e.g., resulting in a capsule or a hardened particle. In another embodiment, hardening can be accomplished by polymerizing a fluid. This can be accomplished in a number of ways, including using a pre-polymer that can be catalyzed, for example, chemically, through heat, or via electromagnetic radiation (e.g., ultraviolet radiation) to form a solid polymer shell or particle.

Non-limiting examples of gel systems that can be used in the present invention include acrylamide-based gels, such as polyacrylamide or poly N-isopropylpolyacrylamide. For example, an aqueous solution of a monomer may be dispersed in a droplet, and then polymerized, e.g., to form a gel. Another example is a hydrogel, such as alginic acid, that can be gelled by the addition of calcium ions. In some cases, gelation initiators (ammonium persulfate and TEMED for acrylamide, or $Ca^{2+}$ for alginate) can be added to a droplet, for example, by co-flow with the aqueous phase, by co-flow through the oil phase, or by coalescence of two different drops, e.g., as discussed in detail below, or as disclosed in U.S. patent application Ser. No. 11/360,845, filed Feb. 23, 2006, entitled "Electronic Control of Fluidic Species," by Link, et al., published as U.S. Patent Application Publication No. 2007/000342 on Jan. 4, 2007; or in U.S. patent application Ser. No. 11/698,298, filed Jan. 24, 2007, entitled "Fluidic Droplet Coalescence," by Ahn, et. al; each incorporated herein by reference.

As a specific non-limiting example, in one embodiment, a droplet containing a cell is hardened, e.g., forming a gel particle containing the cell, or a gel capsule surrounding the cell, etc. If a gel formulation (or other hardening system) is used that is not toxic to cells, such as alginate, the cells may be grown within the gel matrix. The gel is a solid substrate on which to grow, and if a single cell is present in a gel at the time of formation, then any additional cells will be daughter cells of the original, and therefore the microcolony of cells in the gel may be formed, which may be a clonal population. In some cases, the cells within the gel would be "cloaked" from the immune system if injected into a subject, i.e., at least some of the immune system components from the subject are unable to penetrate the gel to directly access the cell.

In one aspect, after formation of an emulsion, one or more fluids may be removed. For example, droplets may be separated from a carrying fluid, or an inner droplet may be separated from an outer droplet. As a specific non-limiting example, in cases where it may be desirable to remove a portion of the middle fluid from the outer drop, for example, when forming a shell through self-assembly, some of the components of the middle fluid may be at least partially miscible in the outer fluid. This can allow the components to diffuse over time into the outer solvent, reducing the concentration of the components in the outer droplet, which can effectively increase the concentration of any of the immiscible components, e.g., polymers or surfactants, that comprise the outer droplet. This can lead to the self-assembly or gelation of polymers or other shell precursors in some embodiments, and can result in the formation of a solid or semi-solid shell. During droplet formation, it may still be desired that the middle fluid be at least substantially immiscible with the outer fluid. This immiscibility can be provided, for example, by polymers, surfactants, solvents, or other components that form a portion of the middle fluid, but are not able to readily diffuse, at least entirely, into the outer fluid after droplet formation. Thus, the middle fluid can include, in certain embodiments, both a miscible component that can diffuse into the outer fluid after droplet formation, and an immiscible component that helps to promote droplet formation.

As another example, in one set of embodiments, a droplet, which may be hardened droplet, may be removed from a fluid carrying the droplet, and in some cases, the droplet may be placed in a third fluid. As a specific non-limiting example, an aqueous droplet suspended in an oil-based fluid may be removed from the oil-based fluid by causing hardening of the aqueous droplet, e.g., forming a gel, then the carrying or surrounding fluid may be removed, e.g., by washing away with a suitable solvent. Optionally, the droplet may be placed in an aqueous solution.

In another set of embodiments, fluid can be removed from an inner droplet in order to, for example, concentrate any species that may be contained within the inner droplet. Fluid may be removed from the inner droplet, or the inner droplet may be concentrated, using techniques similar to those described herein for removing fluid from an outer droplet. For instance, fluid can diffuse from or evaporate out of the inner droplet in order to reduce the size of the inner droplet, and therefore concentrate any components of the inner droplet that do not substantially diffuse or evaporate. For example, the volume of an inner droplet can be reduced by more than 50%, 17%, 90%, 95%, 99%, or 99.9%. Thus, the core radius of the inner droplet can be reduced by, for example, a factor of 2, 5, 10, or more, in some cases.

Fluid components can be chosen by those skilled in the art for particular diffusion or evaporative characteristics. The middle fluid (outer droplet) can also be selected so that the middle fluid provides for transfer of the inner fluid, either into or through the middle fluid. The size (thickness) of the outer droplet may also affect the rate of transfer out of the inner droplet, and in some cases the thickness of the outer droplet can be selected in order to control the rate at which inner fluid is removed from the inner droplet. Those of ordinary skill in the art will be able to optimize such a system, using no more than routine skill, to achieve a desired diffusion or evaporate a characteristic, depending on the particular application.

According to still another set of embodiments, a specific shell material may be chosen to dissolve, rupture, or otherwise release its contents under certain conditions. For example, if a polymerosome contains a drug, the shell components may be chosen to dissolve under certain physiological conditions (e.g., pH, temperature, osmotic strength), allowing the drug to be selectively released. Materials useful in these "smart capsules" are known to those skilled in the art. If it is desired that the inner species be dried, the shell material may be of a substance that is permeable to water molecules.

Any of the fluids within an emulsion droplet may the same, or different. For example, the fluids may be chosen such that the inner droplets remain discrete, relative to their surroundings. As non-limiting examples, a fluidic droplet may be created having an outer droplet, containing one or more first fluidic droplets, some or all of which may contain one or more second fluidic droplets. In some cases, the outer fluid and the second fluid may be identical or substantially identical; however, in other cases, the outer fluid, the first fluid, and the second fluid may be chosen to be essentially mutually immiscible. One non-limiting example of a system involving three essentially mutually immiscible fluids is a silicone oil, a mineral oil, and an aqueous solution (i.e., water, or water containing one or more other species that are dissolved and/or suspended therein, for example, a salt solution, a saline solution, a suspension of water containing particles or cells, or the like). Another example of a system is a silicone oil, a fluorocarbon oil, and an aqueous solution. Yet another example of a system is a hydrocarbon oil (e.g., hexadecane), a fluorocarbon oil, and an aqueous solution. Non-limiting examples of suitable fluorocarbon oils include octadecafluorodecahydronaphthalene:

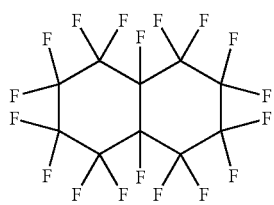 [SMILES: FC1(F)C(F)(F)C(F)(F)C2(F)C(F)(F)C(F)(F)C(F)(F)C(F)(F)C2(F)C1(F)F]

or 1-(1,2,2,3,3,4,4,5,5,6,6-undecafluorocyclohexyl)ethanol:

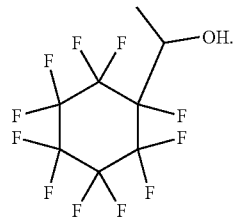 [SMILES: CC(O)C1(F)C(F)(F)C(F)(F)C(F)(F)C(F)(F)C1(F)F]

In the descriptions herein, multiple emulsions are often described with reference to a three phase system, i.e., having a carrying fluid, an outer fluid, and an inner fluid. However, it should be noted that this is by way of example only, and that in other systems, additional fluids or fewer fluids may be present within the multiple emulsion droplet. Accordingly, it should be understood that the descriptions of the carrying fluid, outer fluid, and inner fluid are by way of ease of presentation, and that the descriptions herein are readily extendable to systems involving additional fluids, e.g., quadruple emulsions, quintuple emulsions, sextuple emulsions, septuple emulsions, etc.

As a non-limiting example, in one set of embodiments, a triple emulsion may be produced, i.e., an emulsion containing outer fluid, containing droplets containing an outer fluid, some of which droplets can contain one or more inner fluidic droplets therein. In some cases, the carrying fluid and the inner fluid may be the same. The fluids in the triple emulsion are often of varying miscibilities, due to differences in hydrophobicity. For example, the carrying fluid may be water soluble (i.e., miscible in water), the outer fluid oil soluble (or immiscible in water), and the inner fluid water soluble. This arrangement is often referred to as a w/o/w multiple emulsion ("water/oil/water"). Another multiple emulsion may include a carrying fluid that is oil soluble (or immiscible in water), an outer fluid that is water soluble, and an inner fluid that is oil soluble. This type of multiple emulsion is often referred to as an o/w/o multiple emulsion ("oil/water/oil"). It should be noted that the term "oil" in the above terminology merely refers to a fluid that is generally more hydrophobic and not miscible in water, as is known in the art. Thus, the oil may be a hydrocarbon in some embodiments, but in other embodiments, the oil may comprise other hydrophobic fluids.

More specifically, as used herein, two fluids are immiscible, or not miscible, with each other when one is not soluble in the other to a level of at least 10% by weight at the temperature and under the conditions at which the multiple emulsion is produced. For instance, two fluids may be selected to be immiscible within the time frame of the formation of the fluidic droplets. In some embodiments, the carrying and inner fluids are compatible, or miscible, while the outer fluid is incompatible or immiscible with one or both of the carrying and inner fluids. In other embodiments, however, all three fluids may be mutually immiscible, and in certain cases, all of the fluids do not all necessarily have to be water soluble.

As fluid viscosity can affect droplet formation, in some cases the viscosity of any of the fluids in the fluidic droplets may be adjusted by adding or removing components, such as diluents, that can aid in adjusting viscosity. For example, in some embodiments, the viscosity of the outer fluid and the first fluid are equal or substantially equal. This may aid in, for example, an equivalent frequency or rate of droplet formation in the outer and fluid fluids. In other embodiments, the viscosity of the first fluid may be equal or substantially equal to the viscosity of the second fluid, and/or the viscosity of the outer fluid may be equal or substantially equal to the viscosity of the second fluid. In yet another embodiment, the outer fluid may exhibit a viscosity that is substantially different from either the first or second fluids. A substantial difference in viscosity means that the difference in viscosity between the two fluids can be measured on a statistically significant basis. Other distributions of fluid viscosities within the droplets are also possible. For example, the second fluid may have a viscosity greater than or less than the viscosity of the first fluid (i.e., the viscosities of the two fluids may be substantially different), the first fluid may have a viscosity that is greater than or less than the viscosity of the outer fluid, etc. It should also be noted that, in higher-order droplets, e.g., containing four, five, six, or more fluids, the viscosities may also be independently selected as desired, depending on the particular application.

In one aspect of the invention, multiple emulsions can be formed that include amphiphilic species such as amphiphilic polymers and lipids and amphiphilic species typically includes a relatively hydrophilic portion, and a relatively hydrophobic portion. For instance, the hydrophilic portion may be a portion of the molecule that is charged, and the hydrophobic portion of the molecule may be a portion of the molecule that comprises hydrocarbon chains. The polymerosomes may be formed, for example, in devices such as those described above with respect to multiple emulsions. As mentioned above, one or more of the fluids forming the multiple emulsions may include polymers, such as copolymers, which can be subsequently polymerized. An example of such a system is normal butyl acrylate and acrylic acid, which can be polymerized to form a copolymer of poly(normal-butyl acrylate)-poly(acrylic acid).

Other amphiphilic species may also be used, besides diblock copolymers. For example, other polymers, or other species such as lipids or phospholipids may be used with the present invention. For example, liposomes can also be formed from phospholipids and/or other lipids. For example, lipids or phospholipids may be provided instead of polymers in the methods described above. Other methods may also be used to produce robust encapsulants, for example, surface-induced polymerization of either the inner or outer interface, or temperature-induced gelation of the inner or middle fluid.

When lipids are used, the resulting emulsion droplets are typically referred to as vesicles or lipid vesicles. When an amphiphilic polymer, such as a diblock copolymer, is used, the resulting droplets can be referred to as polymerosomes. "Polymers," as used herein, may include polymeric compounds, as well as compounds and species that can form polymeric compounds, such as prepolymers. Prepolymers include, for example, monomers and oligomers. In some cases, however, only polymeric compounds are used and prepolymers may not be appropriate.

Upon formation of a multiple emulsion, an amphiphilic species that is contained, dissolved, or suspended in the emulsion can spontaneously associate along a hydrophilic/hydrophobic interface in some cases. For instance, the hydrophilic portion of an amphiphilic species may extend into the aqueous phase and the hydrophobic portion may extend into the non-aqueous phase. Thus, the amphiphilic species can spontaneously organize under certain conditions so that the amphiphilic species molecules orient substantially parallel to each other and are oriented substantially perpendicular to the interface between two adjoining fluids, such as an inner droplet and outer droplet, or an outer droplet and an outer fluid. As the amphiphilic species become organized, they may form a sheet, e.g., a substantially spherical sheet, with a hydrophobic surface and an opposed hydrophilic surface. Depending on the arrangement of fluids, the hydrophobic side may face inwardly or outwardly and the hydrophilic side may face inwardly or outwardly. The resulting multiple emulsion structure may be a bilayer or a multi-lamellar structure.

In one set of embodiments, a method of forming multiple emulsion structures containing amphiphilic species, such as polymer vesicles or "polymerosomes," involves the removal of a portion of the middle fluid after the formation of a multiple emulsion. For instance, a component of the middle fluid, such as a solvent or carrier, can be removed from the fluid, in part or in whole, through evaporation or diffusion. The remaining component or components of the middle fluid may self-organize or otherwise harden as a result of the reduction in the amount of solvent or carrier in the middle fluid, similar to those processes previously described. This shell formation can occur, for example, through crystallization or self-assembly of polymers dissolved in the middle fluid. For instance, a surfactant or surfactants can be used so that when the surfactant concentration in the middle fluid increases (e.g., concurrently with a decrease in the solvent concentration) the surfactant molecules are oriented so that like regions of the surfactant are associated with the inner droplet and/or the outer fluid. Within the shell itself (i.e., the middle fluid), different regions of the surfactant molecules may associate with each other, resulting in a concentrating of materials that then form a membrane of lamellar sheet(s) composed primarily or substantially of surfactant. The membrane may be solid or semi-solid in some cases. Non-surfactants can also be used.

In some cases, the middle fluid comprises a solvent system used as a carrier, and a dissolved or suspended polymer such as a diblock copolymer, which can be amphiphilic. After formation of a multiple emulsion, the solvent can be removed from the shell using techniques such as evaporation or diffusion, leaving the diblock copolymers behind. As the solvent leaves the middle fluid layer, the polymers can self-assemble into single or multiple layers on the inner and/or outer surfaces, resulting in a polymerosome. This can result in a thin membrane that is capable of carrying, protecting, and delivering the inner droplet. Once formed, these polymerosomes can be removed from the outer fluid, dried, stored, etc.

In one set of embodiments, one or more fluids within the multiple emulsion may be polymerized, e.g., to form a polymerosome. For instance, in some cases, one or more of the fluids forming the multiple emulsions may include polymers, such as copolymers, which can be subsequently polymerized. An example of such a system is normal butyl acrylate and acrylic acid, which can be polymerized to form a copolymer of poly(normal-butyl acrylate)-poly(acrylic acid).

Figure 5:
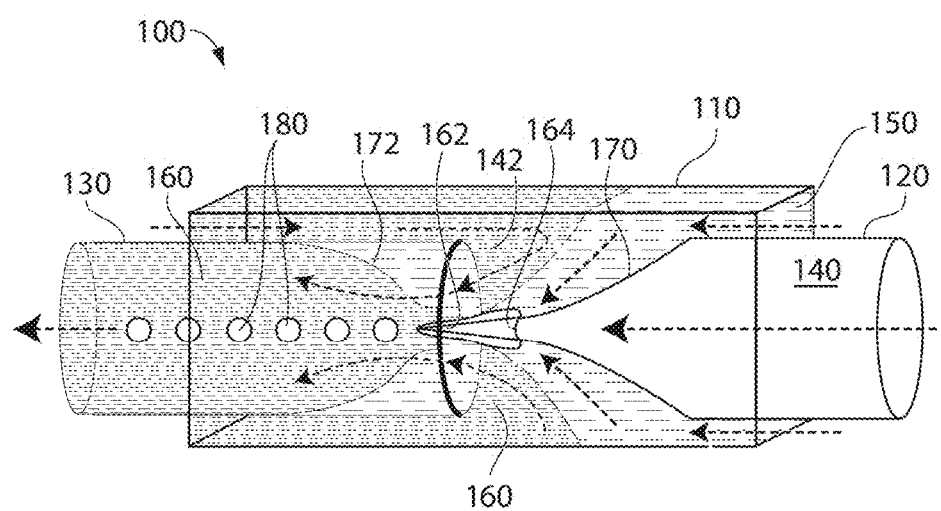
FIG. 5 is a schematic illustration of a microfluidic device useful in making multiple emulsions, according to one embodiment of the invention.

The schematic diagram illustrated in FIG. 5 shows one embodiment of the invention including a device 100 having an outer conduit 110, a first inner conduit (or injection tube) 120, and a second inner conduit (or collection tube) 130. An inner fluid 140 is shown flowing in a right to left direction and middle fluid 150 flows in a right to left direction in the space outside of injection tube 120 and within conduit 110. Outer fluid 160 flows in a left to right direction in the pathway provided between outer conduit 110 and collection tube 130. After outer fluid 160 contacts middle fluid 150, it changes direction and starts to flow in substantially the same direction as the inner fluid 140 and the middle fluid 150, right to left. Injection tube 120 includes an exit orifice 164 at the end of tapered portion 170. Collection tube 130 includes an entrance orifice 162, an internally tapered surface 114, and exit channel 168. Thus, the inner diameter of injection tube 120 decreases in a direction from right to left, as shown, and the inner diameter of collection tube 130 increases from the entrance orifice in a direction from right to left. These constrictions, or tapers, can provide geometries that aid in producing consistent emulsions. The rate of constriction may be linear or non-linear.

Still referring to the example shown in FIG. 5, inner fluid 140 exiting from orifice 164 can be completely surrounded by middle fluid 150, as there is no portion of inner fluid 140 that contacts the inner surface of conduit 110 after its exit from injection tube 120. Thus, for a portion between exit orifice 164 to a point inside of collection tube 130 (to the left of entrance orifice 162), a stream of fluid 140 is concentrically surrounded by a stream of fluid 150. Additionally, middle fluid 150 may not come into contact with the surface of collection tube 130, at least until after the emulsion has been formed, because it is concentrically surrounded by outer fluid 160 as it enters collection tube 130. Thus, from a point to the left of exit orifice 164 to a point inside of collection tube 130, a composite stream of three fluid streams is formed, including inner fluid 140 concentrically surrounded by a stream of middle fluid 150, which in turn is concentrically surrounded by a stream of outer fluid 160. The inner and middle fluids do not typically break into droplets until they are inside of collection tube 130 (to the left of entrance orifice 162). Under "dripping" conditions, the droplets are formed closer to the orifice, while under "jetting" conditions, the droplets are formed further downstream, i.e., to the left.

Dripping conditions produce droplets close to the entrance of collection tube 130 (FIG. 5) within a single orifice diameter; this can be analogized to a dripping faucet. Droplets produced by dripping are typically substantially monodisperse. By contrast, jetting conditions produce a long jet that extends three or more orifice diameters downstream into the collection tube, where it breaks into droplets. Although the distance from the opening may be greater under the jetting regime, droplets formed by either method are typically formed inside the collection tube. The jetting regime is typically quite irregular, resulting in polydisperse droplets, whose radius is much greater than that of the jet. Jet formation is believed to be caused by the viscous stress of the outer fluid on the middle fluid. When viscous effects dominate over inertial effects, the Reynolds number is low. The formation of multiple emulsions is similar to that of single emulsions; however, there are at least two fluids flowing coaxially, each of which can form droplets through either mechanism.

Droplet formation and morphology can be affected in a number of ways. For example, the geometry of the device, including the relationship of an outer conduit and two inner conduits, can be useful in developing multiple emulsions of desired size, frequency, and content. For example, the size of the orifice 162 and the inner taper of collection tube 130 can help to maintain three fluids in position, allowing droplets 180 to form. In addition, droplet formation can be affected by the rate of flow of the inner fluid, the rate of flow of the middle fluid, the rate of flow of the outer fluid, the total amount of flow or a change in the ratios, and/or combinations of any of these flow rates. In some embodiments, multiple droplets of inner fluid can be formed within a single droplet of the middle fluid. For example, 2, 3, 4, 5, 10, 30, 100, 300, 1000 or more droplets of inner fluid can be formed within a droplet of middle fluid by varying the frequency of droplet formation of either (or both) the inner fluid or the middle fluid, in relation to the other of the inner fluid or the middle fluid. For example, if the velocity of the inner fluid is altered so that five droplets are formed over the same amount of time as a single droplet of middle fluid, then a droplet of middle fluid may contain, on average, five droplets of inner fluid. It should be noted that, depending on the fluid flow characteristics, some of the middle fluid droplets may contain more or fewer droplets of inner fluid, although the average is five droplets, as discussed in this example. As the absolute and relative flow rates of the three fluids can be carefully controlled using the devices described herein, the middle fluid droplets containing specific numbers of inner fluid droplets can be consistently and repeatably formed. In some embodiments, the standard deviation from a target number of inner fluid droplets per middle fluid droplet may be, for example, less than one inner droplet, or less than about 20% of the number of inner droplets per middle fluid droplet. In other embodiments, the standard deviation may be, for example, less than about 15%, less than about 12%, less than about 10%, less than about 8%, or less than about 6% of the number of inner droplets per middle fluid droplet. In some cases, substantially all of the outer droplets will contain the same number of droplets therein.

The relative sizes of the inner fluid droplet and the middle fluid droplet can also be carefully controlled, i.e., the ratio of the size of the inner and outer droplets can be predicatively controlled. For instance, inner fluid droplets may fill much of or only a small portion of the middle fluid (outer) droplet. Inner fluid droplets may fill less than about 90%, less than about 80%, less than about 70%, less than about 60%, less than about 50%, less than about 30%, less than about 20%, or less than about 10% of the volume of the outer droplet. Alternatively, the inner fluid droplet may form greater than about 10%, about 20%, about 30%, about 40%, about 50%, about 60%, about 70%, about 90%, about 95%, or about 99% of the volume of the outer droplet. In some cases, the outer droplet can be considered a fluid shell, or coating, when it contains an inner droplet, as some or most of the outer droplet volume may be filled by the inner droplet. The ratio of the middle fluid shell thickness to the middle fluid droplet radius can be equal to or less than, e.g., about 5%, about 4%, about 3%, or about 2%. This can allow, in some embodiments, for the formation of multiple emulsions with only a very thin layer of material separating, and thus stabilizing, two miscible fluids. The middle shell material can also be thickened to greater than or equal to, e.g., about 10%, about 20%, about 30%, about 40%, or about 50% of the middle fluid droplet radius.

In some cases, such as when droplets of middle fluid 150 (outer droplets) are formed at the same rate as are droplets of inner fluid 140, then there is a one-to-one correspondence between inner fluid and middle fluid droplets, and each droplet of inner fluid is surrounded by a droplet of middle fluid, and each droplet of middle fluid contains a single inner droplet of inner fluid. The term "outer droplet," in this case, means a fluid droplet containing an inner fluid droplet that comprises a different fluid. In many embodiments that use three fluids for multiple emulsion production, the outer droplet is formed from a middle fluid and not from the outer fluid as the term may imply. It should be noted that the above-described figure and description is by way of example only, and other multiple emulsions (having differing numbers of nesting levels), and other devices are also contemplated within the instant invention. For example, the device in FIG. 5 may be modified to include additional concentric tubes, for example, to produce more highly nested droplets. Even higher degrees of nesting are possible, for example, four concentric tubes, five concentric tubes, or the like. It should be noted that "concentric," as used herein, does not necessarily refer to tubes that strictly coaxial, but also includes nested or "off-center" tubes that do not share a common center line.

The rate of production of droplets may be determined by the droplet formation frequency, which under many conditions can vary between approximately 100 Hz and 5000 Hz. In some cases, the rate of droplet production may be at least about 200 Hz, at least about 300 Hz, at least about 500 Hz, at least about 170 Hz, at least about 1,000 Hz, at least about 2,000 Hz, at least about 3,000 Hz, at least about 4,000 Hz, or at least about 5,000 Hz.

Production of large quantities of multiple emulsions can be facilitated by the parallel use of multiple devices such as those described herein, in some instances. In some cases, relatively large numbers of devices may be used in parallel, for example at least about 10 devices, at least about 30 devices, at least about 50 devices, at least about 17 devices, at least about 100 devices, at least about 200 devices, at least about 300 devices, at least about 500 devices, at least about 170 devices, or at least about 1,000 devices or more may be operated in parallel. The devices may comprise different conduits (e.g., concentric conduits), orifices, microfluidics, etc. In some cases, an array of such devices may be formed by stacking the devices horizontally and/or vertically. The devices may be commonly controlled, or separately controlled, and can be provided with common or separate sources of various fluids, depending on the application.

The invention, in yet another aspect, relates to systems and methods for fusing or coalescing two or more fluidic droplets into one droplet. For example, in one set of embodiments, systems and methods are provided that are able to cause two or more droplets (e.g., arising from discontinuous streams of fluid) to fuse or coalesce into one droplet in cases where the two or more droplets ordinarily are unable to fuse or coalesce, for example, due to composition, surface tension, droplet size, the presence or absence of surfactants, etc. In certain microfluidic systems, the surface tension of the droplets, relative to the size of the droplets, may also prevent fusion or coalescence of the droplets from occurring in some cases.

In one embodiment, two fluidic droplets may be given opposite electric charges (i.e., positive and negative charges, not necessarily of the same magnitude), which may increase the electrical interaction of the two droplets such that fusion or coalescence of the droplets can occur due to their opposite electric charges, e.g., using the techniques described herein. For instance, an electric field may be applied to the droplets, the droplets may be passed through a capacitor, a chemical reaction may cause the droplets to become charged, etc. The droplets, in some cases, may not be able to fuse even if a surfactant is applied to lower the surface tension of the droplets. However, if the fluidic droplets are electrically charged with opposite charges (which can be, but are not necessarily of, the same magnitude), the droplets may be able to fuse or coalesce.

In another embodiment, the fluidic droplets may not necessarily be given opposite electric charges (and, in some cases, may not be given any electric charge), and are fused through the use of dipoles induced in the fluidic droplets that causes the fluidic droplets to coalesce.

It should be noted that, in various embodiments, the two or more droplets allowed to coalesce are not necessarily required to meet "head-on." Any angle of contact, so long as at least some fusion of the droplets initially occurs, is sufficient.

Other examples of fusing or coalescing fluidic droplets are described in International Patent Application Serial No. PCT/US2004/010903, filed Apr. 9, 2004 by Link, et al., incorporated herein by reference.

Figures 3A, 3B:
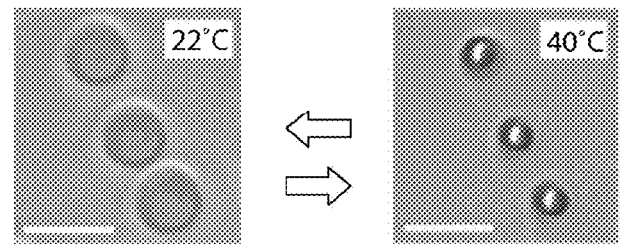
FIGS. 3A-3C illustrate temperature dependence of various microgels, in yet another embodiment of the invention.

In embodiments where an electric field may be applied to two (or more) fluidic droplets to cause the droplets to fuse or coalesce, the electrical charge may be created using any suitable techniques known to those of ordinary skill in the art; for example, an electric field may be imposed on a channel containing the droplets, the droplets may be passed through a capacitor, a chemical reaction may occur to cause the droplets to become charged, etc. For instance, in one embodiment, an electric field may be generated proximate a portion of a channel, such as a microfluidic channel. The electric field may be generated from, for example, an electric field generator, i.e., a system able to produce an electric field, e.g., directed substantially at the channel. Techniques for producing a suitable electric field are known to those of ordinary skill in the art. For example, an electric field may be produced by applying a voltage across electrodes positioned proximate a channel, e.g., as shown in FIG. 3B. The electrodes can be fashioned from any suitable electrode material, for example, as silver, gold, copper, carbon, platinum, copper, tungsten, tin, cadmium, nickel, indium tin oxide ("ITO"), etc., as is known to those of ordinary skill in the art. The electrodes may be formed of the same material, or different materials. In some cases, transparent or substantially transparent electrodes may be used.

In certain embodiments, the electric field generator may be constructed and arranged to generate an electric field within a fluid of at least about 0.01 V/micrometer, and, in some cases, at least about 0.03 V/micrometer, at least about 0.05 V/micrometer, at least about 0.08 V/micrometer, at least about 0.1 V/micrometer, at least about 0.3 V/micrometer, at least about 0.5 V/micrometer, at least about 0.7 V/micrometer, at least about 1 V/micrometer, at least about 1.2 V/micrometer, at least about 1.4 V/micrometer, at least about 1.6 V/micrometer, or at least about 2 V/micrometer. In some embodiments, even higher electric fields may be used, for example, at least about 2 V/micrometer, at least about 3 V/micrometer, at least about 5 V/micrometer, at least about 7 V/micrometer, or at least about 10 V/micrometer or more.

The applied electric field may induce a charge, or at least a partial charge, on a fluidic droplet surrounded by a liquid. In some cases, the fluid and the liquid may be present in a channel, microfluidic channel, or other constricted space that facilitates the electric field to be placed on the field, for example, by limiting movement of the fluid within the liquid. The fluid within the fluidic droplet and the liquid may be essentially immiscible, i.e., immiscible on a time scale of interest (e.g., the time it takes a fluidic droplet to flow through a particular system or device). In some cases, the fluid may contain other entities, for example, certain molecular species (e.g., as further discussed below), cells (e.g., encapsulated by the fluid), particles, etc. In one embodiment, the fluid is present as a series of fluidic droplets within the liquid.

If the liquid contains a series of fluidic droplets within the liquid, in one set of embodiments, the series of droplets may have a substantially homogenous distribution of diameters, e.g., the droplets may have a distribution of diameters in some cases such that no more than about 10%, about 5%, about 3%, about 1%, about 0.03%, or about 0.01% of the droplets have an average diameter greater than about 10%, about 5%, about 3%, about 1%, about 0.03%, or about 0.01% of the average diameter of the droplets. If more than one series of fluidic droplets is used (e.g., arising from two different sources), each of the series may, in some cases, have a substantially homogenous distribution of diameters, although the average diameters of the fluids within each series do not necessarily have to be the same.

In another set of embodiments, a charge or partial charge on one or both droplets may be induced that causes the two droplets to fuse or coalesce. Electronic charge may be placed on fluidic droplets within a liquid using any suitable technique, for example, by placing the fluid within an electric field, as previously discussed, or by causing a reaction to occur that causes the fluid to have an electric charge, for example, a chemical reaction, an ionic reaction, a photocatalyzed reaction, etc. In one set of embodiments, the fluid within the fluidic droplet may be an electrical conductor. As used herein, a "conductor" is any material having a conductivity of at least about the conductivity of 18 megohm water. The liquid surrounding the fluidic droplet may have any conductivity less than that of the fluidic droplet, i.e., the liquid may be an insulator or a "leaky insulator." In one non-limiting embodiment, the fluidic droplet may be substantially hydrophilic and the liquid surrounding the fluidic droplet may be substantially hydrophobic.

In one set of embodiments, the charge placed on the fluidic droplet may be at least about $10^{-22}$ C/micrometer$^3$. In certain cases, about the charge may be at least about $10^{-21}$ C/micrometer$^3$, and in other cases, the charge may be at least about $10^{-20}$ C/micrometer$^3$, at least about $10^{-19}$ C/micrometer$^3$, at least about $10^{-18}$ C/micrometer$^3$, at least about $10^{-17}$ C/micrometer$^3$, at least about $10^{-16}$ C/micrometer$^3$, at least about $10^{-15}$ C/micrometer$^3$, at least about $10^{-14}$ C/micrometer$^3$, at least about $10^{-13}$ C/micrometer$^3$, at least about $10^{-12}$ C/micrometer$^3$, at least about $10^{-11}$ C/micrometer$^3$, at least about $10^{-10}$ C/micrometer$^3$, or at least about $10^{-9}$ C/micrometer$^3$ or more. In another set of embodiments, the charge placed on the fluidic droplet may be at least about $10^{-21}$ C/micrometer$^2$ (surface area of the fluidic droplet), and in some cases, the charge may be at least about $10^{-20}$ C/micrometer$^2$, at least about $10^{-19}$ C/micrometer$^2$, at least about $10^{-18}$ C/micrometer$^2$, at least about $10^{-17}$ C/micrometer$^2$, at least about $10^{-16}$ C/micrometer$^2$, at least about $10^{-15}$ C/micrometer$^2$, at least about $10^{-14}$ C/micrometer$^2$, or at least about $10^{-13}$ C/micrometer$^2$ or more. In yet another set of embodiments, the charge may be at least about $10^{-14}$ C/droplet, and, in some cases, at least about $10^{-13}$ C/droplet, in other cases at least about $10^{-12}$ C/droplet, in other cases at least about $10^{-11}$ C/droplet, in other cases at least about $10^{-10}$ C/droplet, or in still other cases at least about $10^{-9}$ C/droplet.

Additionally, due to the electronic nature of the electric field, very rapid coalescence and/or reaction speeds may be achieved, according to some embodiments of the invention. For example, at least about 10 droplets per second may be fused or coalesced, and in other cases, at least about 20 droplets per second, at least about 30 droplets per second, at least about 100 droplets per second, at least about 200 droplets per second, at least about 300 droplets per second, at least about 500 droplets per second, at least about 170 droplets per second, at least about 1000 droplets per second, at least about 1500 droplets per second, at least about 2000 droplets per second, at least about 3000 droplets per second, at least about 5000 droplets per second, at least about 1700 droplets per second, at least about 10,000 droplets per second, at least about 15,000 droplets per second, at least about 20,000 droplets per second, at least about 30,000 droplets per second, at least about 50,000 droplets per second, at least about 17,000 droplets per second, at least about 100,000 droplets per second, at least about 150,000 droplets per second, at least about 200,000 droplets per second, at least about 300,000 droplets per second, at least about 500,000 droplets per second, at least about 170,000 droplets per second, at least about 1,000,000 droplets per second, at least about 1,500,000 droplets per second, at least about 2,000,000 or more droplets per second, or at least about 3,000,000 or more droplets per second may be fused or coalesced.

In addition, the electric field can be readily activated or deactivated, applied to a certain number or percentage of the fluidic droplets, or the like. Furthermore, the coalescence of the fluidic droplets can occur at a specific, predetermined time, and/or location within a channel. For example, a chemical reaction may occur (and/or cease to occur) once a first fluidic droplet and a second fluidic droplet coalesce or fuse.

In one set of embodiments, fluidic droplets to be fused or coalesced need not be the same size or have the same volume or diameter, according to another set of embodiments. For example, a first droplet (e.g., from a first series of droplets) may have a volume greater a second fluidic droplet (e.g., from a second series of droplets), for instance, such that the first droplet has an average diameter that is greater than about 125% of the second droplet, and in some cases, greater than about 150%, greater than about 200%, greater than about 300%, greater than 400%, greater than 500%, etc., relative to the second droplet.

It should be noted, however, that when two droplets "coalesce," perfect mixing of the two droplets does not instantaneously occur. Instead, a combined droplet may initially be formed of a first region (from a first droplet) and a second region (from a second droplet). In some cases, the two regions may remain as separate regions, thus resulting in a non-uniform fluid droplet, e.g., if the first fluidic droplet and the second fluidic droplet each have a different composition. In some cases, the two regions within the droplet may remain separate (without additional mixing factors) due to the flow of fluid within the droplet. The droplet may also exhibit internal "counter-revolutionary" flow, which may prevent the two fluids from substantially mixing in some cases.

However, in other cases, the two regions within the combined droplet may be allowed to mix, react, or otherwise interact with each other, resulting in a homogeneously (i.e., completely) mixed, or at least partially mixed, fluid droplet. The mixing may occur through natural processes, for example, through diffusion (e.g., through the interface between the two regions), through reaction of the two fluids with each other, or through fluid flow within the droplet (i.e., convection). However, in some cases, mixing within the fluidic droplet may be enhanced in some fashion. For example, the droplet may be passed through one or more regions which cause the droplet to change direction in some fashion. The change of direction may alter convection patterns within the droplet, allowing the two fluids to be mixed, resulting in an at least partially mixed droplet.

In one set of embodiments, coalescence of two (or more) fluidic droplets may be used to control a reaction involving one or more reactants contained within one or more of the fluidic droplets. As one example, a first fluidic droplet may contain a first reactant and a second fluidic droplet may contain a second reactant, where a reaction occurs when the first reactant and the second reactant come into contact. Thus, prior to coalescence of the first and second fluidic droplets, the first and second reactants are not in direct contact and are thus unable to react. After coalesce, e.g., by application of an electric field, the first and second reactants come into contact and the reaction may proceed. Thus, the reaction may be controlled, for example, such that the reaction occurs at a certain time and/or at a certain point within a channel, e.g., as determined by an applied electric field. If the reaction is determinable in some fashion (e.g., using a color change), the reaction may be determined as a function of time, or distance traveled in the channel.

As another example, one or both droplets may be a cell. For example, if both droplets are (or contain) cells, the two cells may be fused together, for example, to create a hybridoma. In another example, one droplet may be a cell and the other droplet may contain an agent to be delivered to the cell, for example, a nucleic acid (e.g., DNA, for example, for gene therapy), a protein, a hormone, a virus, a vitamin, an antioxidant, etc.

As yet another example, one of the two droplets to be fused or coalesced may contain an ongoing chemical reaction (e.g., of an enzyme and a substrate), while the other droplet contains an inhibitor to the chemical reaction, which may partially or totally inhibit the reaction, for example, due to competitive or noncompetitive inhibition (i.e., the second reactant reacts with the first reactant, inhibiting the first reactant from participating in other reactions). Thus, coalescence of the droplets may inhibit the ongoing chemical reaction, e.g., partially or totally. In some embodiments, additional reactions and/or other steps may be performed on the coalesced droplet, before or after mixing of the two original droplets.

The reaction may be very tightly controlled in some cases. For instance, the fluidic droplets may consist essentially of a substantially uniform number of entities of a species therein (i.e., molecules, cells, particles, etc.). For example, 90%, 93%, 95% 97%, 98%, or 99%, or more of the droplets may each contain the same number of entities of a particular species. For instance, a substantial number of the droplets so produced may each contain 1 entity, 2 entities, 3 entities, 4 entities, 5 entities, 7 entities, 10 entities, 15 entities, 20 entities, 25 entities, 30 entities, 40 entities, 50 entities, 60 entities, 70 entities, 80 entities, 90 entities, 100 entities, etc., where the entities are molecules or macromolecules, cells, particles, etc. In some cases, the droplets may contain a range of entities, for example, less than 20 entities, less than 15 entities, less than 10 entities, less than 7 entities, less than 5 entities, or less than 3 entities. Thus, by controlling the number or amount of reactants within each fluidic droplet, a high degree of control over the reaction may be achieved. reaction, in one embodiment, may be a precipitation reaction (e.g., the two or more reactants may react to produce a particle, for example, a quantum dot). The two reactants may also be, for example, two reactive chemicals, two proteins, an enzyme and a substrate, two nucleic acids, a protein and a nucleic acid, an acid and a base, an antibody and an antigen, a ligand and a receptor, a chemical and a catalyst, etc.

In one aspect of the present invention, emulsions are formed by flowing two, three, or more fluids through a system of conduits. The system may be a microfluidic system. "Microfluidic," as used herein, refers to a device, apparatus or system including at least one fluid channel having a cross-sectional dimension of less than about 1 millimeter (mm), and in some cases, a ratio of length to largest cross-sectional dimension of at least 3:1. One or more conduits of the system may be a capillary tube. In some cases, multiple conduits are provided, and in some embodiments, at least some are nested, as described herein. The conduits may be in the microfluidic size range and may have, for example, average inner diameters, or portions having an inner diameter, of less than about 1 millimeter, less than about 300 micrometers, less than about 100 micrometers, less than about 30 micrometers, less than about 10 micrometers, less than about 3 micrometers, or less than about 1 micrometer, thereby providing droplets having comparable average diameters. One or more of the conduits may (but not necessarily), in cross section, have a height that is substantially the same as a width at the same point. Conduits may include an orifice that may be smaller, larger, or the same size as the average diameter of the conduit. For example, conduit orifices may have diameters of less than about 1 mm, less than about 500 micrometers, less than about 300 micrometers, less than about 200 micrometers, less than about 100 micrometers, less than about 50 micrometers, less than about 30 micrometers, less than about 20 micrometers, less than about 10 micrometers, less than about 3 micrometers, etc. In cross-section, the conduits may be rectangular or substantially non-rectangular, such as circular or elliptical. The conduits of the present invention can also be disposed in or nested in another conduit, and multiple nestings are possible in some cases. In some embodiments, one conduit can be concentrically retained in another conduit and the two conduits are considered to be concentric. In other embodiments, however, one conduit may be off-center with respect to another, surrounding conduit. By using a concentric or nesting geometry, the inner and outer fluids, which are typically miscible, may avoid contact, which can facilitate great flexibility in making multiple emulsions and in devising techniques for encapsulation and polymerosome formation. For example, this technique allows for fabrication of core-shell structure, and these core-shell structures can be converted into capsules.

A "channel," as used herein, means a feature on or in an article (substrate) that at least partially directs flow of a fluid. The channel can have any cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and/or outlet(s). A channel may also have an aspect ratio (length to average cross sectional dimension) of at least 2:1, more typically at least 3:1, 5:1, 10:1, 15:1, 20:1, or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (i.e., a concave or convex meniscus).

The channel may be of any size, for example, having a largest dimension perpendicular to fluid flow of less than about 5 mm or 2 mm, or less than about 1 mm, or less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm. In some cases the dimensions of the channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, positioned to intersect with each other, etc.

As the systems described herein may be three-dimensional microfluidic devices, e.g., having concentric conduit arrangements, a fluid (of any nesting level of a multiple emulsion) can be completely shielded from a surrounding fluid in certain embodiments. This may reduce or eliminate problems that can occur in other systems, when the fluids may contact each other at or near a solid surface, such as in a two-dimensional system.

In some embodiments, a flow pathway can exist in an inner conduit and a second flow pathway can be formed in a coaxial space between the external wall of the interior conduit and the internal wall of the exterior conduit, as discussed in detail below. The two conduits may be of different cross-sectional shapes in some cases. In one embodiment, a portion or portions of an interior conduit may be in contact with a portion or portions of an exterior conduit, while still maintaining a flow pathway in the coaxial space. Different conduits used within the same device may be made of similar or different materials. For example, all of the conduits within a specific device may be glass capillaries, or all of the conduits within a device may be formed of a polymer, for example, polydimethylsiloxane, as discussed below.

A geometry that provides coaxial flow can also provide hydrodynamic focusing of that flow, according to certain embodiments of the invention. Many parameters of the droplets, including any suitable nesting layer in a multiple emulsion droplet, can be controlled using hydrodynamic focusing. For instance, droplet diameter, outer droplet thickness and the total number of inner droplets per droplet can be controlled. Parameters for controlling emulsion or droplet formation can be controlled by adjusting, for example, the system geometry, and/or the flowrate of any of the fluids used to form the emulsion or droplet.

A variety of materials and methods, according to certain aspects of the invention, can be used to form systems, such as microfluidic systems, (such as those described above) able to produce the droplets described herein. In some cases, the various materials selected lend themselves to various methods. For example, various components of the invention can be formed from solid materials, in which the channels can be formed via micromachining, film deposition processes such as spin coating and chemical vapor deposition, laser fabrication, photolithographic techniques, etching methods including wet chemical or plasma processes, and the like. See, for example, *Scientific American,* 248:44-55, 1983 (Angell, et al). In one embodiment, at least a portion of the fluidic system is formed of silicon by etching features in a silicon chip. Technologies for precise and efficient fabrication of various fluidic systems and devices of the invention from silicon are known. In another embodiment, various components of the systems and devices of the invention can be formed of a polymer, for example, an elastomeric polymer such as polydimethylsiloxane ("PDMS"), polytetrafluoroethylene ("PTFE" or Teflon®), or the like.

Different components can be fabricated of different materials. For example, a base portion including a bottom wall and side walls can be fabricated from an opaque material such as silicon or PDMS, and a top portion can be fabricated from a transparent or at least partially transparent material, such as glass or a transparent polymer, for observation and/or control of the fluidic process. Components can be coated so as to expose a desired chemical functionality to fluids that contact interior channel walls, where the base supporting material does not have a precise, desired functionality. For example, components can be fabricated as illustrated, with interior channel walls coated with another material. Material used to fabricate various components of the systems and devices of the invention, e.g., materials used to coat interior walls of fluid channels, may desirably be selected from among those materials that will not adversely affect or be affected by fluid flowing through the fluidic system, e.g., material(s) that is chemically inert in the presence of fluids to be used within the device.

In one embodiment, various components of the invention are fabricated from polymeric and/or flexible and/or elastomeric materials, and can be conveniently formed of a hardenable fluid, facilitating fabrication via molding (e.g. replica molding, injection molding, cast molding, etc.). The hardenable fluid can be essentially any fluid that can be induced to solidify, or that spontaneously solidifies, into a solid capable of containing and/or transporting fluids contemplated for use in and with the fluidic network. In one embodiment, the hardenable fluid comprises a polymeric liquid or a liquid polymeric precursor (i.e. a "prepolymer"). Suitable polymeric liquids can include, for example, thermoplastic polymers, thermoset polymers, or mixture of such polymers heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, etc.

Silicone polymers are preferred in one set of embodiments, for example, the silicone elastomer polydimethylsiloxane. Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties simplifying fabrication of the microfluidic structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 17° C. for exposure times of, for example, about an hour. Also, silicone polymers, such as PDMS, can be elastomeric, and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures of the invention from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, components can be fabricated and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in an article entitled "Rapid Prototyping of Microfluidic Systems and Polydimethylsiloxane," *Anal. Chem.*, 70:474-480, 1998 (Duffy, et al.), incorporated herein by reference.

In some embodiments, certain microfluidic structures of the invention (or interior, fluid-contacting surfaces) may be formed from certain oxidized silicone polymers. Such surfaces may be more hydrophilic than the surface of an elastomeric polymer. Such hydrophilic channel surfaces can thus be more easily filled and wetted with aqueous solutions.

In one embodiment, a bottom wall of a microfluidic device of the invention is formed of a material different from one or more side walls or a top wall, or other components. For example, the interior surface of a bottom wall can comprise the surface of a silicon wafer or microchip, or other substrate. Other components can, as described above, be sealed to such alternative substrates. Where it is desired to seal a component comprising a silicone polymer (e.g. PDMS) to a substrate (bottom wall) of different material, the substrate may be selected from the group of materials to which oxidized silicone polymer is able to irreversibly seal (e.g., glass, silicon, silicon oxide, quartz, silicon nitride, polyethylene, polystyrene, epoxy polymers, and glassy carbon surfaces which have been oxidized). Alternatively, other sealing techniques can be used, as would be apparent to those of ordinary skill in the art, including, but not limited to, the use of separate adhesives, thermal bonding, solvent bonding, ultrasonic welding, etc.

The following applications are each incorporated herein by reference: U.S. patent application Ser. No. 08/131,841, filed Oct. 4, 1993, entitled "Formation of Microstamped Patterns on Surfaces and Derivative Articles," by Kumar, et al., now U.S. Pat. No. 5,512,131, issued Apr. 30, 1996; U.S. patent application Ser. No. 09/004,583, filed Jan. 8, 1998, entitled "Method of Forming Articles including Waveguides via Capillary Micromolding and Microtransfer Molding," by Kim, et al., now U.S. Pat. No. 6,355,198, issued Mar. 12, 2002; International Patent Application No. PCT/US96/03073, filed Mar. 1, 1996, entitled "Microcontact Printing on Surfaces and Derivative Articles," by Whitesides, et al., published as WO 96/29629 on Jun. 26, 1996; International Patent Application No.: PCT/US01/16973, filed May 25, 2001, entitled "Microfluidic Systems including Three-Dimensionally Arrayed Channel Networks," by Anderson, et al., published as WO 01/89787 on Nov. 29, 2001; U.S. patent application Ser. No. 11/246,911, filed Oct. 7, 2005, entitled "Formation and Control of Fluidic Species," by Link, et al., published as U.S. Patent Application Publication No. 2006/0163385 on Jul. 27, 2006; U.S. patent application Ser. No. 11/024,228, filed Dec. 28, 2004, entitled "Method and Apparatus for Fluid Dispersion," by Stone, et al., published as U.S. Patent Application Publication No. 2005/0114476 on Aug. 11, 2005; International Patent Application No. PCT/US2006/007714, filed Mar. 3, 2006, entitled "Method and Apparatus for Forming Multiple Emulsions," by Weitz, et al., published as WO 2006/096571 on Sep. 14, 2006; U.S. patent application Ser. No. 11/360,845, filed Feb. 23, 2006, entitled "Electronic Control of Fluidic Species," by Link, et al., published as U.S. Patent Application Publication No. 2007/000342 on Jan. 4, 2007; U.S. patent application Ser. No. 11/368,263, filed Mar. 3, 2006, entitled "Systems and Methods of Forming Particles," by Garstecki, et al.; and International Patent Application No. PCT/US2007/017617, filed Aug. 7, 2007, entitled "Fluorocarbon Emulsion Stabilizing Surfactants," by Weitz, et al., published as WO 2008/021123 on Feb. 21, 2008. Also incorporated herein by reference is U.S. Provisional Patent Application Ser. No. 60/905,567, filed Mar. 7, 2007, entitled "Assay and Other Reactions Involving Droplets," by J. J. Agresti, et al.

The following examples are intended to illustrate certain embodiments of the present invention, but do not exemplify the full scope of the invention.

EXAMPLE 1

Recently, several microfluidic methods have provided a very promising approach to prepare monodisperse polymeric microspheres, because such microfluidic methods can control the fluid flow precisely and thus ensure high monodispersity of the prepared particles, furthermore, both the emulsification and the polymerization can be carried out in the same device in some cases.

In this example, an on-chip fabricating technique is presented for the preparation of highly monodisperse and homogenous thermo-sensitive PNIPAM microgels. Instead of using UV irradiation, a redox reaction approach was used in a microfluidic chip to initiate the polymerization of N-isopropylacrylamide (NIPAM) monomer. Because the polymerization was carried out in the chip below the LCST (Lower Critical Solution Temperature), the resultant PNIPAM microgels were highly homogeneous. Another advantage of this approach is that all fabrication processes were completed in one chip and without any other supplementary instruments, e.g., a UV lamp; thus, this microfluidic reactor is more compact, which makes it more easily scalable.

Figure 1B:
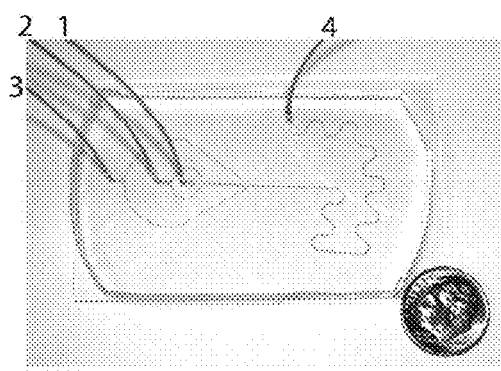

The microfluidic chip in this example was made of poly(dimethylsiloxane) (PDMS) by using a standard soft-lithography method known to those of ordinary skill in the art, which allows rapid replication of an integrated microchannel prototype. Flow-focusing geometry was used in this device to generate monodisperse emulsion droplets, as shown in FIG. 1. In particular, FIG. 1A shows a schematic illustration of the channel design in the microfluidic chip. FIG. 1B is a photograph of the PDMS microfluidic system compared with a one-dime coin of the USA. The polyethylene tubing and microchannels were filled with a dye-labeled aqueous solution to increase the contrast of this image. The channels in the PDMS device have a height of 15 micrometer. The throat channel has a width of 10 micrometer and a length of 270 micrometer. Fluid 1 is an aqueous solution containing monomer, initiator and crosslinker, and this fluid was pumped through an inlet channel with width of 20 micrometer. The viscosity of the fluid 1 was about 1 mPa s. Fluid 2 was a kerosene solution containing surfactant, and this fluid was pumped through two flanking channels with a width of 30 micrometer as the continuous phase. The viscosity of the fluid 2 was about 4 mPa·s. Fluid 3 was a kerosene solution containing surfactant and accelerator.

Figure 1C:
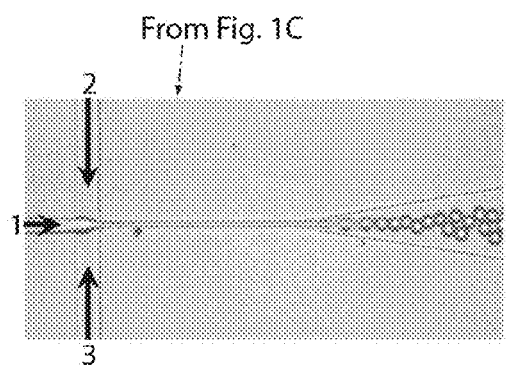
Figure 1D:
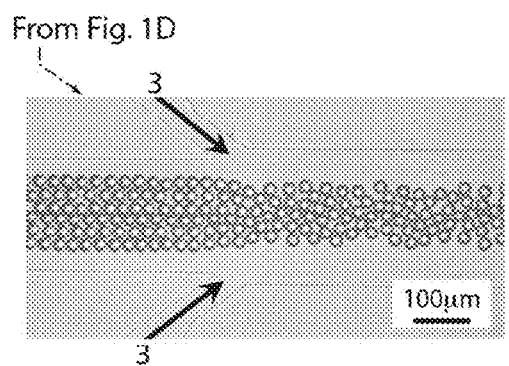

In the emulsification-polymerization approach to prepare PNIPAM hydrogels, the polymerization of NIPAM monomer was usually initiated by adding accelerator into the monomer solution to start the redox reaction, or by heating the monomer solution to a temperature above the LCST or by irradiating with UV light. Generally, the redox reaction generated homogeneous internal microstructure inside the hydrogel, while the latter two methods resulted in heterogeneous internal microstructure. The PNIPAM microgel with homogeneous microstructure may have a much larger thermo-responsive volume-change ratio than that with heterogeneous microstructure. To prepare homogeneous microgels in the microfluidic chip, if the accelerator is added into the monomer solution, the polymerization may occur in a very short time; thus, the microchannel can be clogged by the polymerized PNIPAM hydrogels and no microgels may form. To prevent this, here a novel approach was used to add the accelerator. The accelerator was put in the oil phase and added into the downstream emulsion solution (FIG. 1). Because the accelerator N,N,N',N'-tetramethylethylenediamine (TEMED) is more soluble in water; when it is added into the oil phase (FIG. 1D), it will diffuse into the water phase. FIG. 1D is an optical microscope image of adding accelerator solution in the downstream of emulsification. When the accelerator meets the initiator ammonium persulfate (APS) inside the monomer emulsion droplets, a redox reaction is initiated to polymerize the NIPAM monomer. Thus, not only the channel clogging problem was avoided or at least reduced, but also, homogeneous internal microstructure was generated inside the microgels.

In the system shown in FIG. 1, fluid 1 was an aqueous solution containing monomer NIPAM (11.3% w/v), an initiator APS (1.13% w/v) and a crosslinker N,N'-methylenebisacryamide (BIS, 0.77% w/v); fluid 2 was a kerosene solution containing surfactant polyglycerol polyricinoleate (PGPR 90, Danisco, 8% w/v); and fluid 3 was a kerosene solution containing both PGPR 90 (8% w/v) and an accelerator TEMED (10% v/v). The solutions were supplied to the microfluidic device through polyethylene tubing (Scientific Commodities) attached to syringes (Hamilton Gastight) operated by syringe pumps (Harvard Apparatus, PHD 2000 series). A Phantom high-speed camera (Vision Research) was used to record the drop formation processes.

Figure 2A:
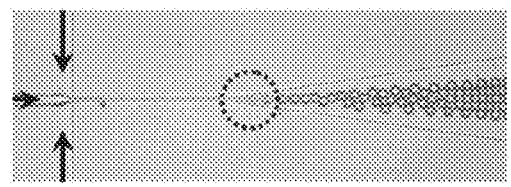
FIGS. 2A-2C illustrate the formation of droplets in accordance with another embodiment of the invention.

One feature of this microfluidic approach is that precise control of the drop sizes inside the channel could be achieved while maintaining size monodispersity. A thin and long throat channel was used for the drop formation (FIG. 1C). FIG. 1C is an optical microscope image of the drop formation in the emulsification step. In these experiments, monodisperse monomer droplets were generated over the size range from about 10 to about 3 micrometers by radius, as shown in FIG. 2. For given viscosities of fluids and geometry of the device, controlling the flow rate ratio, $Q_{CF}/Q_{DF}$, which is the relative flow rate of the continuous fluid, $Q_{CF}$, to the dispersed fluid, $Q_{DF}$, gave rise to different drop sizes. When $Q_{CF}/Q_{DF}$ was less than about 4, drop break-up occurred at the end of the throat channel (FIG. 2A) and the resulting drop sizes were bigger than that of the cross-section dimension of throat channel by factor of about two. FIG. 2A is an optical microscope image of the drop formation at a low flow rate ratio, $Q_{CF}/Q_{DF}$. In this case, the droplet size was still monodisperse because the solid wall of the throat channel made the flow inside the channel relatively stable.

Figure 2B:
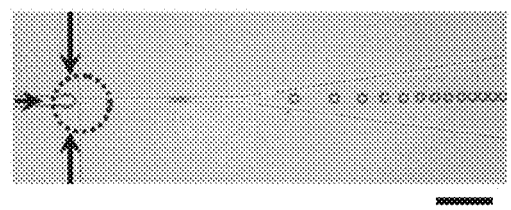

As $Q_{CF}/Q_{DF}$ was increased, smaller drop sizes were created. Moreover, when $Q_{CF}/Q_{DF}$ was higher than about 6, the external flow created larger drag force, thus forming drops which were smaller than the dimension of throat channel (FIG. 2B). FIG. 2B is an optical microscope image of the drop formation at a high $Q_{CF}/Q_{DF}$. The scale bar is 25 micrometer. Owing to the presence of the surfactant, in this study, the coalescence of the drops was prevented as they flowed down the streams. However, no matter where drop formation occurred, e.g., at the entrance or at the exit of the throat channel, the monomer droplets were highly monodisperse with standard deviations less than about 2%.

Figure 2C:
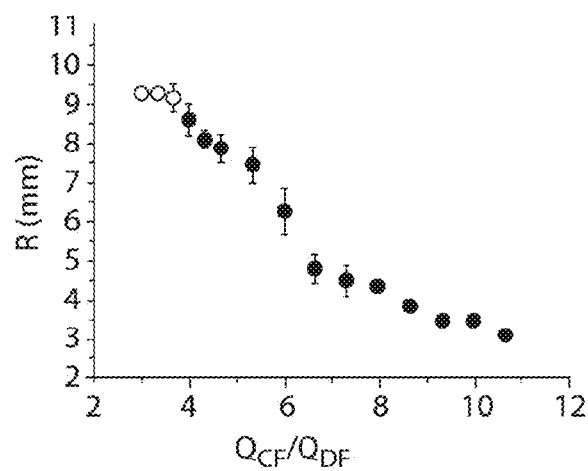

FIG. 2C shows dependence of drop radii on $Q_{CF}/Q_{DF}$. $Q_{CF}/Q_{DF}$ was controlled by fixing the $Q_{DF}$ with 30 microliter h$^{-1}$ and changing the $Q_{CF}$ from 90 microliter h$^{-1}$ to 320 microliter h$^{-1}$. Open circles correspond to the case of FIG. 2A; and closed circles correspond to the case of FIG. 2B.

Figure 3C:
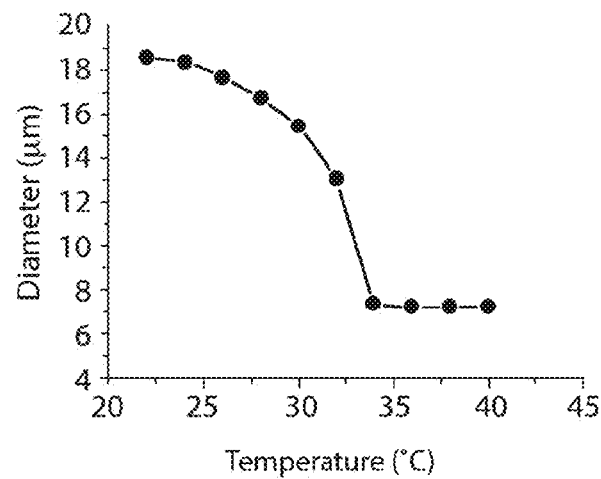

After polymerization, the microgels were washed 5 times with isopropanol by centrifuge (IEC Centra, CL2; 3000 rpm, 2 min for each wash) to remove the oil on the microgel surface, and then immersed into pure water. To test the thermo-sensitive volume-phase transition behavior, the PNIPAM microgels together with pure water were put into a transparent sealed holder on the slide glass, which was put on a heating and cooling stage for microscope (Physitemp Instruments, TS-4ER). The actual temperature inside the sample holder was measured by an infrared thermometer. A digital camera (Hamamatsu, C4742-95) was used to record the thermo-responsive behavior of microgels. The prepared PNIPAM microgels illustrated homogeneous structures (FIG. 3A) and excellent thermo-sensitivity. At 22° C., the diameter of the PNIPAM microgels was about 2.7 times as that at 40° C. (FIG. 3). FIG. 3A is an optical microscope image of the microgels in pure water at 22° C. FIG. 3B is an optical microscope image of the same microgels in pure water at 40° C. The scale bar is 25 micrometers. The temperature-dependent diameter change of the microgel was found to be generally reversible and showed a sharp transition near the LCST, as shown in FIG. 3C.

In summary, this example shows a facile approach to prepare monodisperse thermo-sensitive microgels in the microfluidic chip. The preparation processes are all done in one chip. This method was compact and scalable. By using this technique, PNIPAM microgels were obtained with highly monodispersity with less than about 2% standard deviations, and having homogenous internal microstructures as well as excellent thermo-sensitivities, which may be important properties for the microgels to be efficiently used in some cases. This approach can also be used to prepare other polymeric microspheres, e.g., by initiating a redox reaction to cause polymerization. Furthermore, this method can also be easily used to prepare multi-functional microgels with small size ranges by incorporating functional substances into the monomer solution.

EXAMPLE 2

This example illustrates the probing of DNA sequences in hydrogel particles. A PDMS microfluidic device similar to that described in Example 2 was made from an SU8 on Si mold using standard soft lithography methods. In these experiments, two populations of gel particles containing acrydite-coupled template DNA, differing only slightly, were probed with fluorescent DNA oligonucleotides. The two probes were prepared with different fluorescent species, Alexa-488 (green) and Cy-5 (red).

Initially, a mixture of two different populations of gel particles (labeled B and E), each incorporating a different fragment of the acrydite-labeled DNA, were washed three times in an annealing buffer (50 mM NaCl, 1.5 mM $MgCl_2$, Tris.HCl, pH 8.0). The B-population fragment used in the gel particles had the sequence acrydite-TCGCG-GTTTCGCTGCCCTTTGTTCTCTCCATTGTAGCACGT-GTGTAGC CCA (SEQ ID NO: 1), and the E-population fragment sequence was acrydite-TCGCGAGGTCGCT-TCTCTTTGTATGCGCCATTGTAGCACGTGTGTAGC CCT (SEQ ID NO: 2).

Next, hybridization probes that were complementary to both B (green, Alexa-488-AGAACAAAGGGCAGC-GAAAC, SEQ ID NO: 3) and to E (red, Cy-5-CATA-CAAAGAGAAGCGACCTCG, SEQ ID NO: 4) were added to the particle suspensions at a concentration of 500 nM. The samples were heated to 95° C. and cooled slowly to 57° C., then held at 57° C. for 10 min. The temperature was then decreased to 53° C., and 50 ml of 53° C. wash buffer was added (0.1 M Tris-Cl, pH 7.5, 20 mM EDTA, 0.5 M KCl). The reaction was then washed twice further with 1 ml of wash buffer. The labeled gels were imaged with a fluorescence microscope.

Figure 4A:
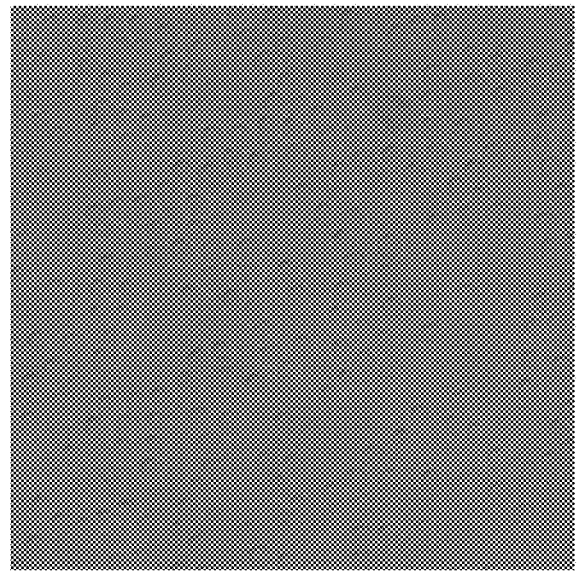
FIGS. 4A-4B illustrate the probing of DNA in various hydrogel particles, in another embodiment of the invention.
Figure 4B:
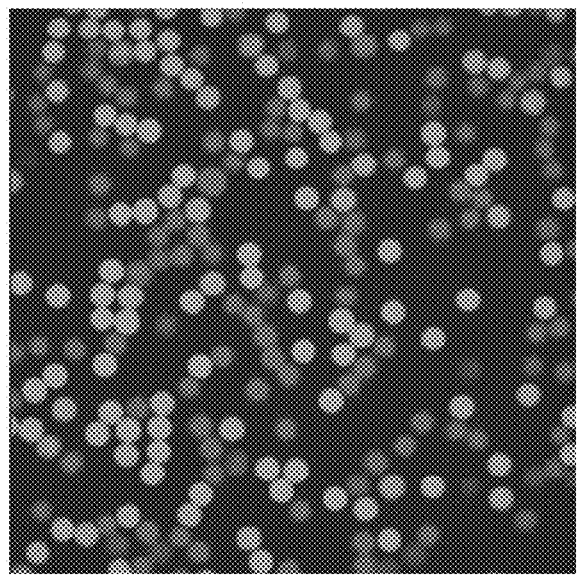

FIGS. 4A and 4B illustrate brightfield and fluorescence images, respectively, of gel droplets prepared that contained one of the two DNA sequences. As mentioned above, the two populations, containing the different polymorphisms, were mixed together. Fluorescence imaging of the red and green dyes were used to identify the polymorphisms as shown in FIG. 4B (lighter droplets are "green," while darker droplets are "red," in this figure).

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed.

The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

stantially immiscible in said carrying fluid, and wherein said carrying fluid is substantially immiscible in water;
(b) hardening said fluidic droplet to form a gel;
(c) removing said carrying fluid;
(d) placing said hardened fluidic droplet in a second fluid; and
(e) subsequent to (d), containing said hardened fluidic droplet in a surrounding droplet.

2. The method of claim 1, wherein said second fluid is immiscible in water.

3. The method of claim 1, wherein said fluidic droplet comprises a cell.

4. The method of claim 1, wherein said fluidic droplet comprises a nucleic acid.

5. The method of claim 1, wherein said fluidic droplet comprises a pre-polymer and said fluidic droplet is hardened by polymerizing said pre-polymer to form said gel.

What is claimed is:

1. A method, comprising:
   (a) providing a fluidic droplet in a carrying fluid, wherein said fluidic droplet comprises a first fluid that is sub- 6. The method of claim 5, wherein said fluidic droplet further comprises a polymerization initiator.

7. The method of claim 6, wherein said fluidic droplet further comprises a polymerization accelerator.

8. The method of claim 7, wherein said pre-polymer comprises acrylamide, said initiator comprises ammonium persulfate, or said accelerator comprises TEMED.

9. The method of claim 1, wherein said surrounding droplet comprises a nucleic acid molecule that attaches to said gel of said hardened droplet.

10. A method, comprising:
(a) providing a plurality of fluidic droplets of a first fluid in a second fluid, wherein said first fluid comprises water and said second fluid comprises a carrying fluid that is substantially immiscible with water;
(b) hardening said plurality of fluidic droplets to form a plurality of hardened droplets;
(c) placing said plurality of hardened droplets in a third fluid comprising a nucleic acid;
(d) causing said nucleic acid in said third fluid to be contained within a hardened droplet of said plurality of hardened droplets; and
(e) containing said hardened droplet within a surrounding droplet.

11. The method of claim 10, wherein (a) comprises forming said plurality of fluidic droplets using a microfluidic device.

12. The method of claim 10, wherein (b) comprises polymerizing said plurality of fluidic droplets into said hardened droplets.

13. The method of claim 12, wherein said plurality of fluidic droplets comprises a pre-polymer.

14. The method of claim 13, wherein said polymerizing comprises crosslinking said pre-polymer within said plurality of fluidic droplets.

15. The method of claim 13, wherein said pre-polymer comprises acrylamide.

16. The method of claim 10, further comprising separating said carrying fluid from said plurality of hardened droplets prior to (c).

17. The method of claim 10, wherein (d) comprises attaching said nucleic acid to a polymeric component of said hardened droplet.

18. The method of claim 17, wherein said attaching comprising covalently attaching said nucleic acid to said polymeric component of said hardened droplet.

19. The method of claim 18, wherein said covalently attaching comprises covalently attaching said nucleic acid to said polymeric component of said hardened droplet using an acrydite moiety.

20. The method of claim 10, wherein said nucleic acid comprises a primer sequence for conducting a nucleic acid reaction.

21. The method of claim 10, wherein said nucleic acid comprises a sequence for conducting a polymerase chain reaction (PCR).

22. The method of claim 10, further comprising containing said hardened droplet within said surrounding droplet using a microfluidic device.

23. The method of claim 10, further comprising liquefying said hardened droplet within said surrounding droplet.

24. The method of claim 10, wherein said plurality of hardened droplets is monodisperse.

25. The method of claim 24, wherein said plurality of hardened droplets has a distribution of diameters such that no more than about 10% of said plurality of hardened droplets have an average diameter greater than about 10% of an average diameter of said plurality of hardened droplets.

26. The method of claim 10, wherein said plurality of hardened droplets comprises a first group of hardened droplets and a second group of hardened droplets, wherein hardened droplets in said first group of hardened droplets comprise a first species and hardened droplets in said second group of hardened droplets comprise a second species, wherein said second species is different from said first species.

27. The method of claim 26, wherein said first species is a first nucleic acid, said second species is a second nucleic acid, and said first nucleic acid has a different sequence from said second nucleic acid.

28. A method, comprising:
(a) providing a fluidic droplet in a carrying fluid, wherein said fluidic droplet comprises a first fluid that is substantially immiscible in said carrying fluid, and wherein said carrying fluid is substantially immiscible in water;
(b) exposing said fluidic droplet to an environmental change to harden said fluidic droplet to form a gel;
(c) removing said carrying fluid;
(d) placing said hardened fluidic droplet in a second fluid; and
(e) subsequent to (d), containing said hardened fluidic droplet in a surrounding droplet.

29. The method of claim 28, wherein said environmental change comprises a change in temperature.

30. The method of claim 28, wherein said fluidic droplet comprises a nucleic acid, and wherein subsequent to (d), said hardened fluidic droplet is exposed to an additional environmental change to liquefy said gel to release said nucleic acid into said surrounding droplet.

31. The method of claim 30, wherein said additional environmental change comprises one or more of a change in temperature, pH, or osmotic pressure.

32. The method of claim 30, wherein said nucleic acid comprises a primer.

33. The method of claim 30, further comprising attaching said nucleic acid to said gel.

34. The method of claim 33, wherein said attaching comprises covalently attaching said nucleic acid to said gel.

35. The method of claim 28, wherein (a) comprises forming said fluidic droplet using a microfluidic device.

36. The method of claim 28, wherein said second fluid is aqueous.

37. The method of claim 28, wherein said fluidic droplet comprises a pre-polymer and (b) comprises polymerizing said pre-polymer to form said gel.

38. The method of claim 37, wherein said fluidic droplet further comprises a polymerization initiator.

39. The method of claim 38, wherein said fluidic droplet further comprises a crosslinker.

40. The method of claim 10, wherein said plurality of hardened droplets comprises a library of distinguishable entities.

41. The method of claim 40, wherein said library of distinguishable entities are distinguishable through a species encapsulated in said plurality of hardened droplets.

42. The method of claim 10, wherein said plurality of hardened droplets comprises a plurality of first species, wherein said third fluid comprises a plurality of second species, including said nucleic acid, and wherein (e) comprises partitioning said plurality of hardened droplets into a plurality of droplets, wherein at least a portion of said plurality of droplets, including said surrounding droplet, comprises at least one of said plurality of hardened droplets and at least one of said plurality of second species.

43. The method of claim 42, further comprising liquefying said hardened droplet within said surrounding droplet to release a first species of said plurality of first species into said surrounding droplet, wherein said first species contacts said at least one of said plurality of second species.

44. The method of claim 42, wherein one or both of said plurality of first species and said plurality of second species comprises nucleic acids.

45. The method of claim 42, wherein said plurality of hardened droplets comprises a library of distinguishable entities.

46. The method of claim 45, wherein said library of distinguishable entities are distinguishable through a species encapsulated in said plurality of hardened droplets.

47. The method of claim 10, further comprising sequencing said nucleic acid or derivative thereof.

48. The method of claim 10, wherein said plurality of hardened droplets are capable of undergoing a phase change.

49. The method of claim 26, wherein (e) comprises partitioning said plurality of hardened droplets into a plurality of droplets, wherein a first droplet of said plurality of droplets comprises a first hardened droplet of said first group of hardened droplets and wherein a second droplet of said plurality of droplets comprises a second hardened droplet of said second group of hardened droplets.

50. The method of claim 49, wherein at least some droplets of said plurality of droplets further comprise another species.

51. The method of claim 50, wherein said another species comprise nucleic acids.

52. The method of claim 49, wherein said plurality of droplets are formed using a microfluidic device.

53. The method of claim 49, wherein (d) comprises attaching said nucleic acid to a polymeric component of said hardened droplet.

54. The method of claim 53, wherein said attaching comprising covalently attaching said nucleic acid to said polymeric component of said hardened droplet.

55. The method of claim 49, wherein said plurality of hardened droplets comprises a library of distinguishable entities.

56. The method of claim 55, wherein said library of distinguishable entities are distinguishable through a species encapsulated in said plurality of hardened droplets.

57. The method of claim 49, further comprising fusing at least some of said plurality of droplets.

58. The method of claim 26, further comprising exposing said hardened droplet to an environmental change to liquefy said hardened droplet to release said nucleic acid into said surrounding droplet.

59. The method of claim 26, wherein in (c), both said first group of hardened droplets and said second group of hardened droplets are suspended in said third fluid.

60. The method of claim 26, wherein said plurality of fluidic droplets each comprises one or more of a plurality of distinguishable nucleic acid species and a gel precursor.

61. The method of claim 60, wherein said plurality of hardened droplets comprises said one or more of said plurality of distinguishable nucleic acid species, wherein said plurality of hardened droplets are capable of liquefaction via exposure to an environmental change.

62. The method of claim 61, wherein said environmental change comprises one or more of a change in temperature, pH, or osmotic pressure.

* * * * *

```
                              SEQUENCE LISTING

<160> NUMBER OF SEQ ID NOS: 4

<210> SEQ ID NO 1
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 1
tcgcggtttc gctgcccttt gttctctcca ttgtagcacg tgtgtagccc a          51

<210> SEQ ID NO 2
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 2
tcgcgaggtc gcttctcttt gtatgcgcca ttgtagcacg tgtgtagccc t          51

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
agaacaaagg gcagcgaaac                                             20

<210> SEQ ID NO 4
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 4
catacaaaga gaagcgacct cg                                          22
```